US011801282B2

(12) United States Patent
Dasseux

(10) Patent No.: US 11,801,282 B2
(45) Date of Patent: *Oct. 31, 2023

(54) CHARGED LIPOPROTEIN COMPLEXES AND THEIR USES

(71) Applicant: Cerenis Therapeutics Holding S.A., Labege (FR)

(72) Inventor: Jean-Louis Dasseux, Toulouse (FR)

(73) Assignee: Abionyx Pharma SA, Balma (FR)

( * ) Notice: Subject to any disclaimer, the term of this patent is extended or adjusted under 35 U.S.C. 154(b) by 784 days.

This patent is subject to a terminal disclaimer.

(21) Appl. No.: 15/398,219

(22) Filed: Jan. 4, 2017

(65) Prior Publication Data

US 2017/0182121 A1 Jun. 29, 2017

Related U.S. Application Data

(63) Continuation of application No. 14/085,685, filed on Nov. 20, 2013, now Pat. No. 9,567,388, which is a continuation of application No. 13/463,582, filed on May 3, 2012, now Pat. No. 8,617,615, which is a continuation of application No. 11/388,135, filed on Mar. 22, 2006, now Pat. No. 8,206,750.

(60) Provisional application No. 60/665,180, filed on Mar. 24, 2005.

(51) Int. Cl.
| | |
|---|---|
| *A61K 38/17* | (2006.01) |
| *A61K 9/127* | (2006.01) |
| *A61K 49/00* | (2006.01) |
| *A61K 31/685* | (2006.01) |
| *A61K 31/688* | (2006.01) |
| *C07K 14/775* | (2006.01) |
| *A61K 9/00* | (2006.01) |
| *A61K 38/00* | (2006.01) |

(52) U.S. Cl.
CPC ........ *A61K 38/1709* (2013.01); *A61K 9/0095* (2013.01); *A61K 9/127* (2013.01); *A61K 9/1275* (2013.01); *A61K 31/685* (2013.01); *A61K 31/688* (2013.01); *A61K 49/0008* (2013.01); *C07K 14/775* (2013.01); *A61K 38/00* (2013.01)

(58) Field of Classification Search
CPC ................ A61K 31/685; A61K 31/688; A61K 38/1709; A61K 38/00; A61K 49/0008; A61K 9/127; A61K 9/1275; C07K 14/775
See application file for complete search history.

(56) References Cited

U.S. PATENT DOCUMENTS

| 4,466,958 A | 8/1984 | Morrison |
| 5,128,318 A | 7/1992 | Levine et al. |
| 5,231,090 A | 7/1993 | Hsia et al. |
| 5,746,223 A | 5/1998 | Williams |
| 5,948,756 A | 9/1999 | Barenholz et al. |
| 6,017,882 A | 1/2000 | Nelsestuen |
| 6,079,416 A | 6/2000 | Williams |
| 6,514,523 B1 | 2/2003 | Sparks |
| 6,828,306 B2 | 12/2004 | Sparks |
| 7,723,287 B1 | 5/2010 | Savion et al. |
| 8,206,750 B2 | 6/2012 | Dasseux |
| 8,617,615 B2 | 12/2013 | Dasseux |
| 9,567,388 B2 | 2/2017 | Dasseux |
| 2003/0099714 A1 | 5/2003 | Dasseux |
| 2004/0038891 A1 | 2/2004 | Bisgaier et al. |
| 2004/0067873 A1 | 4/2004 | Dasseux et al. |
| 2004/0077541 A1 | 4/2004 | Zhu et al. |
| 2009/0186808 A1 | 7/2009 | Tardif |
| 2012/0232005 A1 | 9/2012 | Dasseux et al. |

FOREIGN PATENT DOCUMENTS

| WO | 1995/008986 | 4/1995 | |
| WO | 2002/009678 | 2/2002 | |
| WO | 2003/029294 | 4/2003 | |
| WO | 2003/068189 | 8/2003 | |
| WO | 2003/096983 | 11/2003 | |
| WO | WO-03096983 A2 * | 11/2003 | ............... A61P 9/12 |

OTHER PUBLICATIONS

Stamler ("Phosphatidylinositol promotes cholesterol transport in vivo" Journal of Lipid Research, 41, 2000, 1214-1221) (Year: 2000).*
Davidson ("The Molecular Basis for the Difference in Charge between Pre-β- and α-migrating High Density Lipoproteins" The Journal of Biological Chemistry, 1994, vol. 269, Issue 12, 8959-8965) (Year: 1994).*
Allen et al., 1989, "Liposomes with Prolonged Circulation Times: Factors Affecting Uptake by Reticuloendothelial and Other Tissues," *Biochimica et Biophysica Acta.*, 1(19):27-35.
Bolin et al., 1994, "Binding of Lecithin:Cholesterol Acyltransferase to Reconstituted High Density Lipoproteins Is Affected by Their Lipid but Not Apolipoprotein Composition," *J. Biol. Chem.* 269(10):7429-7434.
Bolin et al., 1996, "Sphingomyelin Inhibits the Lecithin-Cholesterol Acyltransferase Reaction with Reconstituted High Density Lipoproteins by Decreasing Enzyme Binding," *J. Biol. Chem.* 271(32):19152-19158.
Burgess et al., 2003 "Phosphatidylinositol promotes cholesterol transport and excretion," *Journal of Lipid Research* 44(7):1355-1363.

(Continued)

*Primary Examiner* — Robert J Yamasaki
*Assistant Examiner* — Charles Zoltan Constantine
(74) *Attorney, Agent, or Firm* — Biospark Intellectual Property Law

(57) ABSTRACT

The present disclosure provides charged lipoprotein complexes that include as one component a negatively charged phospholipid that is expected to impart the complexes with improved therapeutic properties.

13 Claims, 4 Drawing Sheets

(56) References Cited

OTHER PUBLICATIONS

Figure 1:
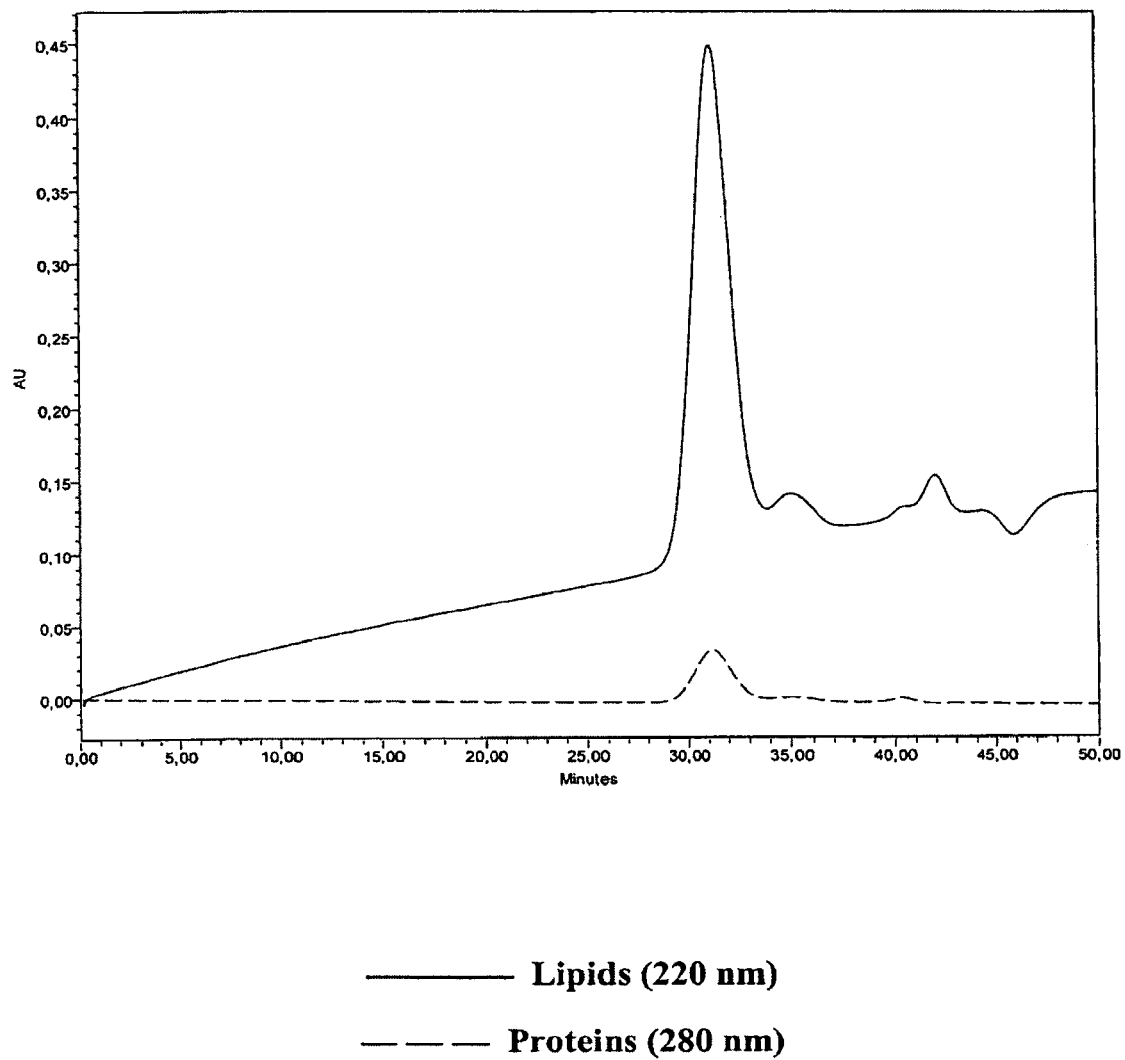

Burgess et al., 2005 "Phosphatidylinositol increases HDL-C levels in humans," *Journal of Lipid Research* 46(2):350-355.
Davidson et al., 1994 "The Molecular Basis for the Difference in Charge between Pre-β-and α-Migrating High Density Lipoproteins," *The Journal of Biological Chemistry*, 269(12):8959-8965.
Examination Report dated Apr. 29, 2009 corresponding to European Application No. 06727346.6.
Extended European Search Report dated Jan. 11, 2011 corresponding to European Application No. 10010660.8.
Fielding et al., 2007, "Reverse Cholesterol Transport—New Roles for Preβ$_1$-HDL and Lecithin:Cholesterol Acyltransferase," High Density Lipoproteins: From Basic Biology to Clinical Aspects, *Christopher J. Fielding, ed.*, pp. 143-161.
Forte et al., 1995, "Recruitment of cell phospholipids and cholesterol by apolipoproteins A-II and A-I: formation of nascent apolipoprotein-specific HDL that differ in size, phospholipid composition, and reactivity with LCAT," *J. Lipid Res.*, 36:148-157.
International Search Report dated Sep. 28, 2006 corresponding to International Application No. PCT/IB2006/000635.
Kee et al., 2002, "Metabolism of ApoA-I as Lipid-Free Protein or as Component of Discoidal and Spherical Reconstituted HDL's Studies in Wild-Type and Hepatic Lipase Transgenic Rabbits," *Arterioscler Thromb Vase Biol.*, 22:1912-1917.
Li et al., 1994, "Analysis of high density lipoproteins by a modified gradient gel electrophoresis method," *Journal of Lipid Research*, 35:1698-1711.

Nyholm et al., 2003, "Properties of Palmitoyl Phosphatidylcholine, Sphingomyelin, and Dihydrosphingomyelin Bilayer Membranes as Reported by Different Fluorescent Reporter Molecules", *Biophysical Journal*, 84(2):987-997.
Papapanagiotou et al., 2001, "Effects of Hormone Replacement Therapy on the Phospholipid Composition of High Density Lipoproteins in Postmenopausal Women", *Journal of Obstetrics and Gynecology*, 21(1):56-61.
PCT Written Opinion of the IPEA dated May 31, 2007 corresponding to International Application No. PCT/IB2006/000635.
Skipski et al., 1964, "Quantitative Analysis of Phospholipids by Thin-Layer Chromatography," *Biochem J.*, 90:374-378.
Sparks et al., 1998, "Effects of the Surface Lipid Composition of Reconstituted LPA-I on Apolipoprotein A-I Structure and Lecithin:Cholesterol Acyltransferase Activity," *Biochimica et Biophysica Acta.*, 1390:160-172.
Stamler et al., 2000, "Phosphatidylinositol Promoted Cholesterol Transport in Vivo", *Journal of Lipid Research*, Bethesda, MD, 41 (8):1214-1221.
Zhang et al., 1998, "Characterization of phospholipids in pre-αHDL: selective phospholipid efflux with apolipoprotein A-I," *J. Lipid Res.*, 39:1601-1607.
Zhao et al., 1996, "Effect of the Apolipoprotein A-I and Surface Lipid Composition of Reconstituted Discoidal HDL on Cholesterol Efflux from Cultured Fibroblasts," *Biochemistry*, 35(51):16510-16518.
Extended European Search Report dated Jan. 18, 2012 corresponding to European Application No. 10010652.5.

\* cited by examiner

CHARGED LIPOPROTEIN COMPLEXES AND THEIR USES

1. CROSS-REFERENCE TO RELATED APPLICATIONS

This application is a continuation of U.S. application Ser. No. 14/085,685, filed Nov. 20, 2013, now allowed, which is a continuation of U.S. application Ser. No. 13/463,582, filed May 3, 2012, now U.S. Pat. No. 8,617,615, issued Dec. 31, 2013, which is a continuation of U.S. application Ser. No. 11/388,135, filed Mar. 22, 2006, now U.S. Pat. No. 8,206,750, issued Jun. 26, 2012, which claims the benefit under 35 U.S.C. § 119(e) to of U.S. provisional application No. 60/665,180, filed Mar. 24, 2005, the contents of each of which are incorporated herein in their entireties by reference thereto in their entirety.

2. TECHNICAL FIELD

The present disclosure provides charged lipoprotein complexes, pharmaceutical compositions comprising the complexes and methods of using the complexes to treat or prevent a variety of conditions and disorders, including dyslipidemia and/or diseases, disorders and/or conditions associated therewith.

3. BACKGROUND

Circulating cholesterol is carried by plasma lipoproteins—complex particles of lipid and protein composition that transport lipids in the blood. Four major classes of lipoprotein particles circulate in plasma and are involved in the fat-transport system: chylomicrons, very low density lipoprotein (VLDL), low density lipoprotein (LDL) and high density lipoprotein (HDL). Chylomicrons constitute a short-lived product of intestinal fat absorption. VLDL and particularly, LDL, are responsible for the delivery of cholesterol from the liver (where it is synthesized or obtained from dietary sources) to extrahepatic tissues, including the arterial walls. HDL, by contrast, mediates reverse cholesterol transport (RCT), the removal of cholesterol lipids, in particular from extrahepatic tissues to the liver, where it is stored, catabolized, eliminated or recycled. HDL also plays a role in inflammation, transporting oxidized lipids and interleukin.

Lipoprotein particles have a hydrophobic core comprised of cholesterol (normally in the form of a cholesteryl ester) and triglycerides. The core is surrounded by a surface coat comprising phospholipids, unesterified cholesterol and apolipoproteins. Apolipoproteins mediate lipid transport, and some may interact with enzymes involved in lipid metabolism. At least ten apolipoproteins have been identified, including: ApoA-I, ApoA-II, ApoA-IV, ApoA-V, ApoB, ApoC-I, ApoC-II, ApoC-III, ApoD, ApoE, ApoJ and ApoH. Other proteins such as LCAT (lecithin:cholesterol acyltransferase), CETP (cholesteryl ester transfer protein), PLTP (phospholipid transfer protein) and PON (paraoxonase) are also found associated with lipoproteins.

Cardiovascular diseases such as coronary heart disease, coronary artery disease and atherosclerosis are linked overwhelmingly to elevated serum cholesterol levels. For example, atherosclerosis is a slowly progressive disease characterized by the accumulation of cholesterol within the arterial wall. Compelling evidence supports the theory that lipids deposited in atherosclerotic lesions are derived primarily from plasma LDLs; thus, LDLs have popularly become known as "bad" cholesterol. In contrast, HDL serum levels correlate inversely with coronary heart disease. Indeed, high serum levels of HDLs are regarded as a negative risk factor. It is hypothesized that high levels of plasma HDLs are not only protective against coronary artery disease, but may actually induce regression of atherosclerotic plaque (see, e.g., Badimon et al., 1992, Circulation 86(Suppl. 11486-94; Dansky and Fisher, 1999, Circulation 100:1762-63; Tangirala et al., 1999, Circulation 100(17): 1816-22; Fan et al., 1999, Atherosclerosis 147(1):139-45; Deckert et al., 1999, Circulation 100(11):1230-35; Boisvert et al., 1999, Arterioscler. Thromb. Vase. Biol. 19(3):525-30; Benoit et al., 1999, Circulation 99(1):105-10; Holvoet et al., 1998, J. Clin. Invest. 102(2):379-85; Duverger et al., 1996, Circulation 94(4):713-17; Miyazaki et al., 1995, Arterioscler. Thromb. Vase. Biol. 15(11):1882-88; Mezdour et al., 1995, Atherosclerosis 113(2):237-46; Liu et al., 1994, J. Lipid Res. 35(12):2263-67; Plump et al., 1994, Proc. Nat. Acad. Sci. USA 91(20):9607-11; Paszty et al., 1994, J. Clin. Invest. 94(2):899-903; She et al, 1992, Chin. Med. J. (Engl). 105(5):369-73; Rubin et al., 1991, Nature 353(6341):265-67; She et al., 1990, Ann. NY Acad. Sci. 598:339-51; Ran, 1989, Chung Hua Ping Li Hsueh Tsa Chih (also translated as: Zhonghua Bing Li Xue Za Zhi) 18(4):257-61; Quezado et al., 1995, J. Pharmacol. Exp. Ther. 272(2):604-11; Duverger et al., 1996, Arterioscler. Thromb. Vase. Biol. 16(12):1424-29; Kopfler et al., 1994, Circulation; 90(3): 1319-27; Miller et al., 1985, Nature 314(6006):109-11; Ha et al., 1992, Biochim. Biophys. Acta 1125(2):223-29; Beitz et al., 1992, Prostaglandins Leukot. Essent. Fatty Acids 47(2):149-52). As a consequence, HDLs have popularly become known as "good" cholesterol, (see, e.g., Zhang, et al., 2003 Circulation 108:661-663).

The "protective" role of HDL has been confirmed in a number of studies (e.g., Miller et al., 1977, Lancet 1(8019): 965-68; Whayne et al., 1981, Atherosclerosis 39:411-19). In these studies, the elevated levels of LDL appear to be associated with increased cardiovascular risk, whereas high HDL levels seem to confer cardiovascular protection. In vivo studies have further demonstrated the protective role of HDL, showing that HDL infusions into rabbits may hinder the development of cholesterol induced arterial lesions (Badimon et al., 1989, Lab. Invest. 60:455-61) and/or induce their regression (Badimon et al., 1990, J. Clin. Invest. 85:1234-41).

3.1 Reverse Cholesterol Transport, HDL and Apolipoprotein A-I

The reverse cholesterol transport (RCT) pathway functions to eliminate cholesterol from most extrahepatic tissues and is crucial to maintaining the structure and function of most cells in the body. RCT consists mainly of three steps: (a) cholesterol efflux, i.e., the initial removal of cholesterol from various pools of peripheral cells; (b) cholesterol esterification by the action of lecithin:cholesterol acyltransferase (LCAT), preventing a re-entry of effluxed cholesterol into cells; and (c) uptake of HDL cholesterol and cholesteryl esters to liver cells for hydrolysis, then recycling, storage, excretion in bile or catabolism to bile acids LCAT, the key enzyme in RCT, is produced by the liver and circulates in plasma associated with the HDL fraction. LCAT converts cell-derived cholesterol to cholesteryl esters, which are sequestered in HDL destined for removal (see Jonas 2000, Biochim. Biophys. Acta 1529(1-3):245-56). Cholesteryl ester transfer protein (CETP) and phospholipid transfer protein (PLTP) contribute to further remodeling of the circulating HDL population. CETP moves cholesteryl esters made by LCAT to other lipoproteins, particularly ApoB-comprising lipoproteins, such as VLDL and LDL.

PLTP supplies lecithin to HDL. HDL triglycerides are catabolized by the extracellular hepatic triglyceride lipase, and lipoprotein cholesterol is removed by the liver via several mechanisms The functional characteristics of HDL particles are mainly determined by their major apolipoprotein components such as ApoA-I and ApoA-II. Minor amounts of ApoC-I, ApoC-II, ApoC-III, ApoD, ApoA-IV, ApoE, ApoJ have also been observed associated with HDL. HDL exists in a wide variety of different sizes and different mixtures of the above-mentioned constituents, depending on the status of remodeling during the metabolic RCT cascade or pathway Each HDL particle usually comprises at least 1 molecule, and usually two to 4 molecules, of ApoA-I. HDL particles may also comprise only ApoE (gamma-LpE particles), which are known to also be responsible for cholesterol efflux, as described by Prof. Gerd Assmann (see, e.g., von Eckardstein et al., 1994, Curr Opin Lipidol. 5(6):404-16). ApoA-I is synthesized by the liver and small intestine as preproapolipoprotein A-I, which is secreted as proapolipoprotein A-I (proApoA-I) and rapidly cleaved to generate the plasma form of ApoA-I, a single polypeptide chain of 243 amino acids (Brewer et al., 1978, Biochem. Biophys. Res. Commun. 80:623-30). PreproApoA-I that is injected experimentally directly into the bloodstream is also cleaved into the plasma form of ApoA-I (Kion et al., 2000, Biophys. J. 79(3):1679-85; Segrest et al., 2000, Curr. Opin. Lipidol. 11(2):105-15; Segrest et al., 1999, J. Biol. Chem. 274 (45):31755-58).

ApoA4 comprises 6 to 8 different 22-amino acid alpha-helices or functional repeats spaced by a linker moiety that is frequently proline. The repeat units exist in amphipathic helical conformation (Segrest et al., 1974, FEBS Lett. 38: 247-53) and confer the main biological activities of ApoA-I, i.e., lipid binding and lecithin cholesterol acyl transferase (LCAT) activation.

ApoA-I forms three types of stable complexes with lipids: small, lipid-poor complexes referred to as pre-beta-1 HDL; flattened discoidal particles comprising polar lipids (phospholipid and cholesterol) referred to as pre-beta-2 HDL; and spherical particles, comprising both polar and nonpolar lipids, referred to as spherical or mature HDL (HDL$_3$ and HDL$_2$). Most HDL in the circulating population comprise both ApoA-I and ApoA-II (the "AI/AII-HDL fraction"). However, the fraction of HDL comprising only ApoA-I (the "AI-HDL fraction") appears to be more effective in RCT. Certain epidemiologic studies support the hypothesis that the Apo-AI-HDL fraction is anti-atherogenic. (Parra et al., 1992, Arterioseler. Thromb. 12:701-07; Decossin et al., 1997, Eur. J. Clin. Invest. 27:299-307).

HDL are made of several populations of particles that have different sizes, lipid composition and apolipoprotein composition. They can be separated according to their properties, including their hydrated density, apolipoprotein composition and charge characteristics. For example, pre-beta-HDL are characterized by a lower surface charge than mature alpha-HDL. Because of this charge difference, pre-beta-HDL and mature alpha-HDL have different electrophoretic mobilities in agarose gel (David et al., 1994, J. Biol. Chem. 269(12):8959-8965).

The metabolism of pre-beta-HDL and mature alpha-HDL also differs. Pre-beta-HDL have two metabolic fates: either removal from plasma and catabolism by the kidney or remodeling to medium-sized HDL that are preferentially degraded by the liver (Lee et al., 2004, J. Lipid Res. 45(4):716-728).

Although the mechanism for cholesterol transfer from the cell surface (i.e., cholesterol efflux) is unknown, it is believed that the lipid-poor complex, pre-beta-1 HDL, is the preferred acceptor for cholesterol transferred from peripheral tissue involved in RCT (see Davidson et al., 1994, J. Biol. Chem. 269:22975-82; Bielicki et al., 1992, J. Lipid Res. 33:1699-1709; Rothblat et al., 1992, J. Lipid Res. 33:1091-97; and Kawano et al., 1993, Biochemistry 32:5025-28; Kawano et al., 1997, Biochemistry 36:9816-25). During this process of cholesterol recruitment from the cell surface, pre-beta-I HDL is rapidly converted to pre-beta-2 HDL. PLTP may increase the rate of pre-beta-2 HDL disc formation, but data indicating a role for PLTP in RCT is lacking. LCAT reacts preferentially with discoidal, small (pre-beta) and spherical (i.e., mature) HDL, transferring the 2-acyl group of lecithin or other phospholipids to the free hydroxyl residue of cholesterol to generate cholesteryl esters (retained in the HDL) and lysolecithin. The LCAT reaction requires ApoA-I as an activator; i.e., ApoA-I is the natural cofactor for LCAT. The conversion of cholesterol sequestered in the HDL to its ester prevents re-entry of cholesterol into the cell, the net result being that cholesterol is removed from the cell.

Cholesteryl esters in the mature HDL particles in the ApoAI-HDL fraction (i.e., comprising ApoA-I and no ApoA-II) are removed by the liver and processed into bile more effectively than those derived from HDL comprising both ApoA-I and ApoA-II (the AI/AII-HDL fraction). This may be owing, in part, to the more effective binding of ApoAI-HDL to the hepatocyte membrane. The existence of an HDL receptor has been hypothesized, and a scavenger receptor, class B, type I (SR-BI) has been identified as an HDL receptor (Acton et al., 1996, Science 271:518-20; Xu et al., 1997, Lipid Res. 38:1289-98). SR-BI is expressed most abundantly in steroidogenic tissues (e.g., the adrenals), and in the liver (Landschulz et al., 1996, J. Clin. Invest. 98:984-95; Rigotti et al., 1996, J. Biol. Chem. 271:33545-49). For a review of HDL receptors, see Broutin et al., 1988, Anal. Biol. Chem. 46:16-23.

Initial lipidation by ATP-binding cassette transporter AI appears to be critical for plasma HDL formation and for ability of pre-beta-HDL particles for cholesterol efflux (Lee and Parks, 2005, Curr. Opin. Lipidol. 16(1): 19-25). According to these authors, this initial lipidation enables pre-beta-HDL to function more efficiently as a cholesterol acceptor and prevents ApoA-I from rapidly associating with pre-existing plasma HDL particles, resulting in greater availability of pre-beta-HDL particles for cholesterol efflux.

CETP may also play a role in RCT. Changes in CETP activity or its acceptors, VLDL and LDL, play a role in "remodeling" the HDL population. For example, in the absence of CETP, the HDLs become enlarged particles that are not cleared. (For reviews of RCT and HDLs, see Fielding and Fielding, 1995, J. Lipid Res. 36:211-28; Barrans et al., 1996, Biochem. Biophys. Acta 1300:73-85; Hirano et al., 1997, Arterioscler. Thromb. Vase. Biol. 17(6): 1053-59).

HDL also plays a role in the reverse transport of other lipids and apolar molecules, and in detoxification, i.e., the transport of lipids from cells, organs, and tissues to the liver for catabolism and excretion. Such lipids include sphingomyelin (SM), oxidized lipids, and lysophophatidylcholine. For example, Robins and Fasulo (1997, J. Clin. Invest. 99:380-84) have shown that HDLs stimulate the transport of plant sterol by the liver into bile secretions.

The major component of HDL, ApoA-I, can associate with SM in vitro. When ApoA-I is reconstituted in vitro with bovine brain SM (BBSM), a maximum rate of reconstitution occurs at 28° C., the temperature approximating the phase transition temperature for BBSM (Swaney, 1983, J. Biol. Chem. 258(2), 1254-59). At BBSM:ApoA-I ratios of 7.5:1 or less (wt/wt), a single reconstituted homogeneous HDL particle is formed that comprises three ApoA-I molecules per particle and that has a BBSM:ApoA-I molar ratio of 360:1. It appears in the electron microscope as a discoidal complex similar to that obtained by recombination of ApoA-I with phosphatidylcholine at elevated ratios of phospholipid/protein. At BBSM:ApoA-I ratios of 15:1 (wt/wt), however, larger-diameter discoidal complexes form that have a higher phospholipid:protein molar ratio (535:1). These complexes are significantly larger, more stable, and more resistant to denaturation than ApoA-I complexes formed with phosphatidylcholine.

Sphingomyelin (SM) is elevated in early cholesterol acceptors (pre-beta-HDL and gamma-migrating ApoE-comprising lipoprotein), suggesting that SM might enhance the ability of these particles to promote cholesterol efflux (Dass and Jessup, 2000, J. Pharm. Pharmacol. 52:731-61; Huang et al., 1994, Proc. Natl. Acad. Sci. USA 91:1834-38; Fielding and Fielding 1995, J. Lipid Res. 36:211-28).

3.2 Protective Mechanism of HDL and ApoA-I

Recent studies of the protective mechanism(s) of HDL have focused on apolipoprotein A-I (ApoA-I), the major component of HDL. High plasma levels of ApoA-I are associated with absence or reduction of coronary lesions (Maciejko et al., 1983, N. Engl. J. Med. 309:385-89; Sedlis et al., 1986, Circulation 73:978-84).

The infusion of ApoA-I or of HDL in experimental animals exerts significant biochemical changes, as well as reduces the extent and severity of atherosclerotic lesions. After an initial report by Maciejko and Mao (1982, Arteriosclerosis 2:407a), Badimon et al., (1989, Lab. Invest. 60:455-61; 1989, J. Clin. Invest. 85:1234-41) found that they could significantly reduce the extent of atherosclerotic lesions (reduction of 45%) and their cholesterol ester content (reduction of 58.5%) in cholesterol-fed rabbits, by infusing HDL (d=1.063–1.325 g/ml). They also found that the infusions of HDL led to a close to a 50% regression of established lesions. Esper et al. (1987, Arteriosclerosis 7:523a) have shown that infusions of HDL can markedly change the plasma lipoprotein composition of Watanabe rabbits with inherited hypercholesterolemia, which develop early arterial lesions. In these rabbits, HDL infusions can more than double the ratio between the protective HDL and the atherogenic LDL.

The potential of HDL to prevent arterial disease in animal models has been further underscored by the observation that ApoA-I can exert a fibrinolytic activity in vitro (Saku et al., 1985, Thromb. Res. 39:1-8). Ronneberger (1987, Xth Int. Congr. Pharmacol., Sydney, 990) demonstrated that ApoA-I can increase fibrinolysis in beagle dogs and in Cynomologous monkeys. A similar activity can be noted in vitro on human plasma. Ronneberger was able to confirm a reduction of lipid deposition and arterial plaque formation in ApoA-I treated animals.

In vitro studies indicate that complexes of ApoA-I and lecithin can promote the efflux of free cholesterol from cultured arterial smooth muscle cells (Stein et al., 1975, Biochem. Biophys. Acta, 380:106-18). By this mechanism, HDL can also reduce the proliferation of these cells (Yoshida et al., 1984, Exp. Mol Pathol. 41:258-66).

Infusion therapy with HDL comprising ApoA-I or ApoA-I mimetic peptides has also been shown to regulate plasma HDL levels by the ABC1 transporter, leading to efficacy in the treatment of cardiovascular disease (see, e.g., Brewer et al., 2004, Arterioscler. Thromb. Vase. Biol. 24:1755-1760).

Two naturally occurring human mutations of ApoA-I have been isolated in which an arginine residue is mutated to cysteine. In apolipoprotein A-$I_{Milano}$ (ApoA-$I_M$), this substitution occurs at residue 173, whereas in apolipoprotein A-$I_{Paris}$ (ApoA-$I_P$), this substitution occurs at residue 151 (Franceschini et al., 1980, J. Clin. Invest. 66:892-900; Weisgraber et al., 1983, J. Biol. Chem. 258:2508-13; Bruckert et al., 1997, Atherosclerosis 128:121-28; Daum et al., 1999, J. Mol. Med. 77:614-22; Klon et al., 2000, Biophys. J. 79(3):1679-85). Reconstituted HDL particles comprising disulfide-linked homodimers of either ApoA-$I_M$ or ApoA-$I_P$ are similar to reconstituted HDL particles comprising wild-type ApoA-I in their ability to clear dimyristoylphosphatidylcholine (DMPC) emulsions and their ability to promote cholesterol efflux (Calabresi et al., 1997b, Biochemistry 36:12428-33; Franceschini et al., 1999, Arterioscler. Thromb. Vase. Biol. 19:1257-62; Daum et al., 1999, J. Mol. Med. 77:614-22). In both mutations, heterozygous individuals have decreased levels of HDL but paradoxically, are at a reduced risk for atherosclerosis (Franceschini et al., 1980, J. Clin. Invest. 66:892-900; Weisgraber et al., 1983, J. Biol. Chem. 258:2508-13; Bruckert et al., 1997, Atherosclerosis 128:121-28). Reconstituted HDL particles comprising either variant are capable of LCAT activation, although with decreased efficiency when compared with reconstituted HDL particles comprising wild-type ApoA-I (Calabresi et al., 1997a, Biochem. Biophys. Res. Commun. 232:345-49; Daum et al., 1999, J. Mol. Med. 77:614-22).

The ApoA-$I_M$ mutation is transmitted as an autosomal dominant trait; eight generations of carriers within a family have been identified (Gualandri et al., 1984, Am. J. Hum. Genet. 37:1083-97). The status of an ApoA-$I_M$ carrier individual is characterized by a remarkable reduction in HDL-cholesterol level. In spite of this, carrier individuals do not apparently show any increased risk of arterial disease. Indeed, by examination of genealogical records, it appears that these subjects may be "protected" from atherosclerosis (Sirtori et al., 2001, Circulation, 103: 1949-1954; Roma et al., 1993, J. Clin. Invest. 91(4):1445-520).

The mechanism of the possible protective effect of ApoA-$I_M$ in carriers of the mutation seems to be linked to a modification in the structure of the mutant ApoA-$I_M$, with loss of one alpha-helix and an increased exposure of hydrophobic residues (Franceschini et al., 1985, J. Biol. Chem. 260:1632-35). The loss of the tight structure of the multiple alpha-helices leads to an increased flexibility of the molecule, which associates more readily with lipids, compared to normal ApoA-I. Moreover, apolipoprotein-lipid complexes are more susceptible to denaturation, thus suggesting that lipid delivery is also improved in the case of the mutant.

Bielicki, et al. (1997, Arterioscler. Thromb. Vase. Biol. 17 (9):1637-43) has demonstrated that ApoA-$I_M$ has a limited capacity to recruit membrane cholesterol compared with wild-type ApoA-I. In addition, nascent HDL formed by the association of ApoA-$I_M$ with membrane lipids was predominantly 7.4-nm particles rather than larger 9- and 11-nm complexes formed by wild-type ApoA-I. These observations indicate that the $Arg_{173} \rightarrow Cys_{173}$ substitution in the ApoA-I primary sequence interfered with the normal process of cellular cholesterol recruitment and nascent HDL assembly. The mutation is apparently associated with a decreased efficiency for cholesterol removal from cells. Its antiatherogenic properties may therefore be unrelated to RCT.

The most striking structural change attributed to the $Arg_{173} \rightarrow Cys_{173}$ substitution is the dimerization of ApoA-$I_M$ (Bielicki et al., 1997, Arterioscler. Thromb. Vasc. Biol. 17 (9):1637-43). ApoA-$I_M$ can form homodimers with itself and heterodimers with ApoA-II. Studies of blood fractions comprising a mixture of apolipoproteins indicate that the presence of dimers and complexes in the circulation may be responsible for an increased elimination half-life of apolipoproteins. Such an increased elimination half-life has been observed in clinical studies of carriers of the mutation (Gregg et al., 1988, NATO ARW on Human Apolipoprotein Mutants: From Gene Structure to Phenotypic Expression, Limone S G). Other studies indicate that ApoA-$I_M$ dimers (ApoA-$I_M$/ApoA-$I_M$) act as an inhibiting factor in the interconversion of HDL particles in vitro (Franceschini et al., 1990, J. Biol. Chem. 265:12224-31).

3.3 Current Treatments for Dyslipidemia and Related Disorders

Dyslipidemic disorders are diseases associated with elevated scrum cholesterol and triglyceride levels and lowered serum HDL:LDL ratios, and include hyperlipidemia, especially hypercholesterolemia, coronary heart disease, coronary artery disease, vascular and perivascular diseases, and cardiovascular diseases such as atherosclerosis. Syndromes associated with atherosclerosis such as intermittent claudication, caused by arterial insufficiency, are also included. A number of treatments are currently available for lowering the elevated serum cholesterol and triglycerides associated with dyslipidemic disorders. However, each has its own drawbacks and limitations in terms of efficacy, side-effects and qualifying patient population.

Bile-acid-binding resins are a class of drugs that interrupt the recycling of bile acids from the intestine to the liver; e.g., cholestyramine (Questran Light®, Bristol-Myers Squibb), and colestipol hydrochloride (Colestid®, The Upjohn Company). When taken orally, these positively-charged resins bind to the negatively charged bile acids in the intestine. Because the resins cannot be absorbed from the intestine, they are excreted carrying the bile acids with them. The use of such resins at best, however, only lowers serum cholesterol levels by about 20%, and is associated with gastrointestinal side-effects, including constipation and certain vitamin deficiencies. Moreover, since the resins bind other drugs, other oral medications must be taken at least one hour before or four to six hours subsequent to ingestion of the resin; thus, complicating heart patient's drug regimens.

Statins are cholesterol lowering agents that block cholesterol synthesis by inhibiting HMGCoA reductase, the key enzyme involved in the cholesterol biosynthetic pathway. Statins, e.g., lovastatin (Mevacor®), simvastatin (Zocor®), pravastatin (Pravachol®), fluvastatin (Lescol®) and atorvastatin (Lipitor®), are sometimes used in combination with bile-acid-binding resins. Statins significantly reduce serum cholesterol and LDL-serum levels, and slow progression of coronary atherosclerosis. However, serum HDL cholesterol levels are only moderately increased. The mechanism of the LDL lowering effect may involve both reduction of VLDL concentration and induction of cellular expression of LDL-receptor, leading to reduced production and/or increased catabolism of LDLs. Side effects, including liver and kidney dysfunction are associated with the use of these drugs (The Physicians Desk Reference, 56$^{th}$ Ed., 2002) Medical Economics).

Niacin (nicotinic acid) is a water soluble vitamin B-complex used as a dietary supplement and antihyperlipidemic agent. Niacin diminishes production of VLDL and is effective at lowering LDL. In some cases, it is used in combination with bile-acid binding resins. Niacin can increase HDL when used at adequate doses, however, its usefulness is limited by serious side effects when used at such high doses. Niaspan® is a form of extended-release niacin that produces fewer side effects than pure niacin. Niacin/Lovastatin (Nicostatin®) is a formulation containing both niacin and lovastatin and combines the benefits of each drug.

Fibrates are a class of lipid-lowering drugs used to treat various forms of hyperlipidemia (i.e., elevated serum triglycerides) that may also be associated with hypercholesterolemia. Fibrates appear to reduce the VLDL fraction and modestly increase HDL—however the effect of these drugs on serum cholesterol is variable. In the United States, fibrates such as clofibrate (Atromid-S®), fenofibrate (Tricor®) and bezafibrate (Bezalip®) have been approved for use as antilipidemic drugs, but have not received approval as hypercholesterolemia agents. For example, clofibrate is an antilipidemic agent that acts (via an unknown mechanism) to lower serum triglycerides by reducing the VLDL fraction. Although serum cholesterol may be reduced in certain patient subpopulations, the biochemical response to the drug is variable, and is not always possible to predict which patients will obtain favorable results. Atromid-S® has not been shown to be effective for prevention of coronary heart disease. The chemically and pharmacologically related drug, gemfibrozil (Lopid®) is a lipid regulating agent that moderately decreases scrum triglycerides and VLDL cholesterol, and moderately increases HDL cholesterol—the $HDL_2$ and $HDL_3$ subtractions as well as both ApoA-I and A-II (i.e., the AI/AMT-HDL fraction). However, the lipid response is heterogeneous, especially among different patient populations. Moreover, while prevention of coronary heart disease was observed in male patients between 40-55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates including toxicity such as malignancy, (especially gastrointestinal cancer), gallbladder disease and an increased incidence in non-coronary mortality.

Oral estrogen replacement therapy may be considered for moderate hypercholesterolemia in post-menopausal women. However, increases in HDL may be accompanied with an increase in triglycerides. Estrogen treatment is, of course, limited to a specific patient population (postmenopausal women) and is associated with serious side effects including induction of malignant neoplasms, gall bladder disease, thromboembolic disease, hepatic adenoma, elevated blood pressure, glucose intolerance, and hypercalcemia.

Other agents useful for the treatment of hyperlipidemia include ezetimibe (Zetia®; Merck), which blocks or inhibits cholesterol absorption. However, inhibitors of ezetimibe have been shown to exhibit certain toxicities.

The need therefore exists for safer drugs that are more efficacious in lowering scrum cholesterol, increasing HDL serum levels, preventing and/or treating dyslipidemia and/or diseases, conditions and/or disorders associated with dyslipidemia.

For example, HDL, as well as recombinant forms of ApoA-I complexed with phospholipids can serve as sinks/scavengers for apolar or amphipathic molecules, e.g., cholesterol and derivatives (oxysterols, oxidized sterols, plant sterols, etc.), cholesterol esters, phospholipids and derivatives (oxidized phospholipids), triglycerides, oxidation products, and lipopolysaccharides (LPS) (see, e.g., Casas et al., 1995, J. Surg. Res. November 59(5):544-52). HDL can also serve as also a scavenger for TNF-alpha and other lymphokines. HDL can also serve as a carrier for human serum paraoxonases, e.g., PON-1,-2,-3. Paraoxonase, an esterase associated with HDL, is important for protecting cell components against oxidation. Oxidation of LDL, which occurs during oxidative stress, appears directly linked to development of atherosclerosis (Aviram, 2000, Free Radic. Res. 33 Suppl:S85-97). Paraoxonase appears to play a role in susceptibility to atherosclerosis and cardiovascular disease (Aviram, 1999, Mol. Med. Today 5(9):381-86). Human serum paraoxonase (PON-1) is bound to high-density lipoproteins (HDLs). Its activity is inversely related to atherosclerosis. PON-1 hydrolyzes organophosphates and may protect against atherosclerosis by inhibition of the oxidation of HDL and low-density lipoprotein (LDL) (Aviram, 1999, Mol. Med. Today 5(9):381-86). Experimental studies suggest that this protection is associated with the ability of PON-1 to hydrolyze specific lipid peroxides in oxidized lipoproteins. Interventions that preserve or enhance PON-1 activity may help to delay the onset of atherosclerosis and coronary heart disease.

HDL further has a role as an antithrombotic agent and fibrinogen reducer, and as an agent in hemorrhagic shock (Cockerill et al., WO 01/13939, published Mar. 1, 2001). HDL, and ApoA-I in particular, has been show to facilitate an exchange of lipopolysaccharide produced by sepsis into lipid particles comprising ApoA-I, resulting in the functional neutralization of the lipopolysaccharide (Wright et al., WO9534289, published Dec. 21, 1995; Wright et al., U.S. Pat. No. 5,928,624 issued Jul. 27, 1999; Wright et al., U.S. Pat. No. 5,932,536, issued Aug. 3, 1999).

The therapeutic use of ApoA-I, ApoA-$I_M$, ApoA-$I_P$ and other variants, as well as reconstituted HDL, is presently limited, however, by the large amount of apolipoprotein required for therapeutic administration and by the cost of protein production, considering the low overall yield of production. It has been suggested by early clinical trials that the dose range is between 1.5-4 g of protein per infusion for treatment of cardiovascular diseases. The number of infusions required for a full treatment is unknown. (See, e.g., Eriksson et al., 1999, Circulation 100(6):594-98; Carlson, 1995, Nutr. Metab. Cardiovasc. Dis. 5:85-91; Nanjee et al., 2000, Arterioscler. Thromb. Vasc. Biol. 20(9):2148-55; Nanjee et al., 1999, Arterioscler. Thromb. Vasc. Biol. 19(4):979-89; Nanjee et al., 1996, Arterioscler. Thromb. Vasc. Biol. 16(9):1203-14). Thus, there is a need to develop new methods for the treatment and/or prevention of dyslipidemic diseases, conditions and/or disorders.

Citation or identification of any reference in Section 2 or in any other section of this application shall not be construed as an admission that such reference is available as prior art to the present invention

4. SUMMARY

The present disclosure provides charged lipoprotein complexes, compositions comprising the complexes and methods of using the complexes to treat and/or prevent a variety of disorders and conditions, including dyslipidemia, and/or the various diseases, disorders and/or conditions associated therewith. The complexes are generally lipoproteins that comprise two fractions, an apolipoprotein fraction and a lipid fraction, and that include as a key ingredient a specified amount of a charged phospholipid (or a mixture of two or more different, typically like-charged, phospholipids). The charged phospholipid(s) can be positively or negatively charged at physiological pH, but in many embodiments are negatively charged. In some embodiments, the charged phospholipid comprises one or more of phosphatidylinositol, phosphatidylserine, phosphatidylglycerol and/or phosphatidic acid.

The apolipoprotein fraction comprises one or more proteins, peptides or peptide analogs that are capable of mobilizing cholesterol when included in the complex (called "apolipoproteins"). A specific example of such an apolipoprotein is ApoA-I. Other specific examples are described further herein below.

The lipid fraction generally comprises one or more neutral phospholipids and the charged phospholidpid, and may optionally include additional lipids, such as for example, triglycerides, cholesterol, cholesterol esters, lysophospholipids, and their various analogs and/or derivatives. In some embodiments, the charged lipoprotein complexes do not include such optional lipids.

The neutral phospholipids(s) can be any phospholipid that has a net charge of about zero at physiological pH. In some embodiments, the neutral phospholipid is a zwitterion that has a net charge of about zero at physiological pH. In some embodiments, the neutral phospholipid comprises a lecithin (also known as phosphatidylcholine or "PC"). In some embodiments the neutral phospholipid comprises a sphingomyelin ("SM"). In some embodiments, the neutral phospholipid comprises a mixture of lecithin and SM. Embodiments of charged lipoprotein complexes in which the lipid fraction comprises either lecithin or SM, at least one charged phospholipid(s), and optionally other lipids, are called "ternary" complexes, because they comprise three "major" components: an apolipoprotein, a lecithin or a sphingomyelin and a charged phospholipid(s). Embodiments of charged lipoprotein complexes in which the lipid fraction comprises both lecithin and SM, at least one charged phospholipids(s) and optionally other lipids are called "quaternary" complexes.

The total amount of charged phospholipids(s) comprising the lipid fraction of the charged lipoprotein complexes can vary, but typically ranges from about 0.2 to 10 wt %. In some embodiments, the lipid fraction comprises from about 0.2 to 2 wt %, 0.2 to 3 wt %, 0.2 to 4 wt %, 0.2 to 5 wt %, 0.2 to 6 wt %, 0.2. to 7 wt %, 0.2 to 8 wt % or 0.2 to 9 wt % total charged phospholipids(s). In some embodiments, the lipid fraction comprises about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 wt % total charged phospholipid(s), and/or a range including any of these values as endpoints. In some embodiments, the lipid fraction comprises from about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 wt % total charged phospholipid(s) up to about 4, 5, 6, 7, 8, 9 or 10 wt % total charged phospholipid(s).

The total amount of neutral phospholipid(s) comprising the lipid fraction can also vary, and will depend upon the amount of charged phospholipid(s) and any optional lipids included. In embodiments which do not include optional lipids, the lipid fraction will generally comprise from about 90 to 99.8 wt % total neutral phospholipid(s).

As mentioned above, the neutral phospholipid can comprise a lecithin, a SM, or a mixture of lecithin, and SM. The lecithin and/or SM can comprise the bulk of the neutral phospholipid or, alternatively, the neutral phospholipid can include neutral phospholipids in addition to the lecithin and/or SM. In embodiments in which the neutral phospholipid includes lecithin but not SM, the neutral phospholipid will typically comprise from about 5 to 100 wt % lecithin. In some embodiments, the neutral phospholipid comprises 100 wt % lecithin.

In embodiments in which the neutral phospholipid comprise SM but not lecithin, the neutral phospholipid will generally comprise from about 5 to 100 wt % SM. In some embodiments, the neutral phospholipid comprises 100 wt % SM.

In embodiments in which the neutral phospholipid includes a mixture of lecithin and SM, both the amount of the mixture comprising the total neutral phospholipid, and the relative amounts of the lecithin and SM comprising the mixture (i.e., lecithin: SM molar ratio) can vary. Typically, the neutral phospholipid will comprise from about 5 to 100 wt % of the lecithin/SM mixture. In some embodiments, the neutral phospholipid is comprised wholly of lecithin and SM (i.e., 100 wt % of a mixture of lecithin and SM).

The molar ratio of lecithin to SM (lecithin:SM) can vary, but will typically range from about 20:1 to 1:20. In some embodiments, the lecithin:SM molar ratio ranges from about 10:3 to 10:6. In other embodiments, the lecithin:SM molar ratio ranges from about 1:20 to 3:10.

Optional lipids, if included, will generally comprise about 50 wt % or less of the lipid fraction. In some embodiments, the lipid fraction comprises less than about 30 wt % total optional lipids. In a specific embodiment, the lipid fraction comprises less than about 5 wt %, 10 wt % or 20 wt % total optional lipids.

The lipid-to-apolipoprotein molar ratio of the charged lipoprotein complexes can also vary. In some embodiments, the charged lipoprotein complexes comprise a lipid:apolipoprotein molar ratio ranging from about 2:1 to about 200:1. In some embodiments, the lipid:apolipoprotein molar ratio is about 50:1.

The charged lipoprotein complexes described herein can take on a variety of shapes, sizes and forms, ranging from micellar structures, to small, discoidal particles that are akin to naturally-occurring pre-beta HDL particles, to larger, discoidal particles that are akin to naturally-occurring alpha-HDL particles, to large, spherical particles that are akin to naturally-occurring $HDL_2$ or $HDL_3$. The desired size and shape of the charged lipoprotein complexes described herein can be controlled by adjusting the components and weight (or molar) ratios of the lipids comprising the lipid fraction, as well as the lipid:apolipoprotein molar ratio, as is know in the art (see, e.g., Barter et al., 1996, J. Biol. Chem. 271: 4243-4250).

In some embodiments, the charged lipoprotein complexes are in the form of discoidal particles in which the lipid fraction consists essentially of about 90 to 99.8 wt % total neutral phospholipid(s) and about 0.2 to 10 wt % total negatively charged phospholipids(s). The discoidal particles can be large (e.g., having an oblate diameter of about 10 to 14 nm) or small (e.g., having an oblate diameter of about 5 to 10 nm). The size of the discoidal particles can be controlled by adjusting the lipid:apolipoprotein molar ratio, as is known in the art (see, e.g., Barter et al., 1996, supra.). The sizes of the particles can be determined using, for example, size exclusion column chromatography.

The pharmaceutical compositions generally comprise charged lipoprotein complexes as described herein, and may optionally include one or more pharmaceutically acceptable carriers, excipients and/or diluents. In some embodiments, the pharmaceutical compositions are packaged in unit dosage amounts suitable for administration. For example, in some embodiments, the compositions comprise unit dosage amounts of dried (for example lyophilized) charged lipoprotein complexes packaged in sealed vials. Such compositions are suitable for reconstitution with water, physiological solution (such as saline) or buffer, and administration via injection. Such compositions may optionally include one or more anti-caking and/or anti-agglomerating agents to facilitate reconstitution of the charged complexes, or one or more buffering agents, sugars or salts (e.g., sodium chloride) designed to adjust the pH, osmolality and/or salinity of the reconstituted suspension.

The charged lipoprotein complexes and compositions described herein are expected to effect and/or facilitate cholesterol efflux and/or elimination, and are therefore expected to be useful in the treatment and/or prophylaxis of a variety of conditions and disorders, including, for example, dyslipidemia and/or diseases, conditions and/or disorders associated with dyslipidemia or with consumption, accumulation or elimination of lipids (e.g., fat deposits, cell degradation)/or apolar molecules such as toxins, xenobiotics, etc. Non-limiting examples of such diseases, disorders and/or associated conditions that can be treated or prevented with the charged lipoprotein complexes and compositions described herein include, peripheral vascular disease, hypertension, inflammation, Alzheimer's disease, restenosis, atherosclerosis, and the myriad clinical manifestations of atherosclerosis, such as, for example, stroke, ischemic stroke, transient ischemic attack, myocardial infarction, acute coronary syndrome, angina pectoris, renovascular hypertension, renovascular insufficiency, intermittent claudication, critical limb ischemia, rest pain and gangrene.

The methods generally involve administering to a subject an amount of a charged lipoprotein complex or pharmaceutical complex described herein effective to treat or prevent the particular indication. The complexes and/or compositions can be administered alone (as monotherapy) or, alternatively, they can be adjunctively administered with other therapeutic agents useful for treating and/or preventing dyslipidemia and/or its associated conditions, diseases and/or disorders. Non-limiting examples of therapeutic agents with which the charged lipoprotein complexes and compositions described herein can be adjunctively administered include bile acid-binding resins, HMG CoA-reductase inhibitors (statins), niacin, resins, inhibitors of cholesterol absorption and fibrates.

While not intending to be bound by any theory of operation, it is believed that the charged phospholipids comprising the lipid fraction will impart the charged lipoprotein complexes and compositions described herein with improved therapeutic properties over conventional lipoprotein complexes. One of the key differences between small discoidal pre-beta HDL, which are degraded in the kidney, and large discoidal and/or spherical HDL, which are recognized by the liver where their cholesterol is either stored, recycled, metabolized (as bile acids) or eliminated (in the bile), is the charge of the particles. The small, discoidal pre-beta HDL have a lower negative surface charge than large, discoidal and/or spherical HDL that are negatively charged. While not intending to be bound by any theory of operation, it is believed that the higher negative charge is one of the factors that triggers the recognition of the particles by the liver, and that therefore avoids catabolism of the particles by the kidney. Owing in part to the presence of the charged phospholipids(s), it is believed that the charged lipoprotein complexes and compositions described herein will stay in the circulation longer than conventional lipoprotein complexes, or that the charge will affect the half-life of the lipoprotein in a charge-dependent manner. It is expected that their longer circulation (residence) time will facilitate cholesterol mobilization (by giving the complexes more time to accumulate cholesterol) and esterification (by providing more time for the LCAT to catalyze the esterification reaction). The charge may also increase the rate of cholesterol capture and/or removal, thereby facilitating removal of cholesterol in larger quantities. As a consequence, it is expected that the charged lipoprotein complexes and compositions described herein will provide therapeutic benefit over conventional lipoprotein therapies, as less complex and/or composition will need to be administered, and less often.

5. BRIEF DESCRIPTION OF THE FIGURES

Figure 2:
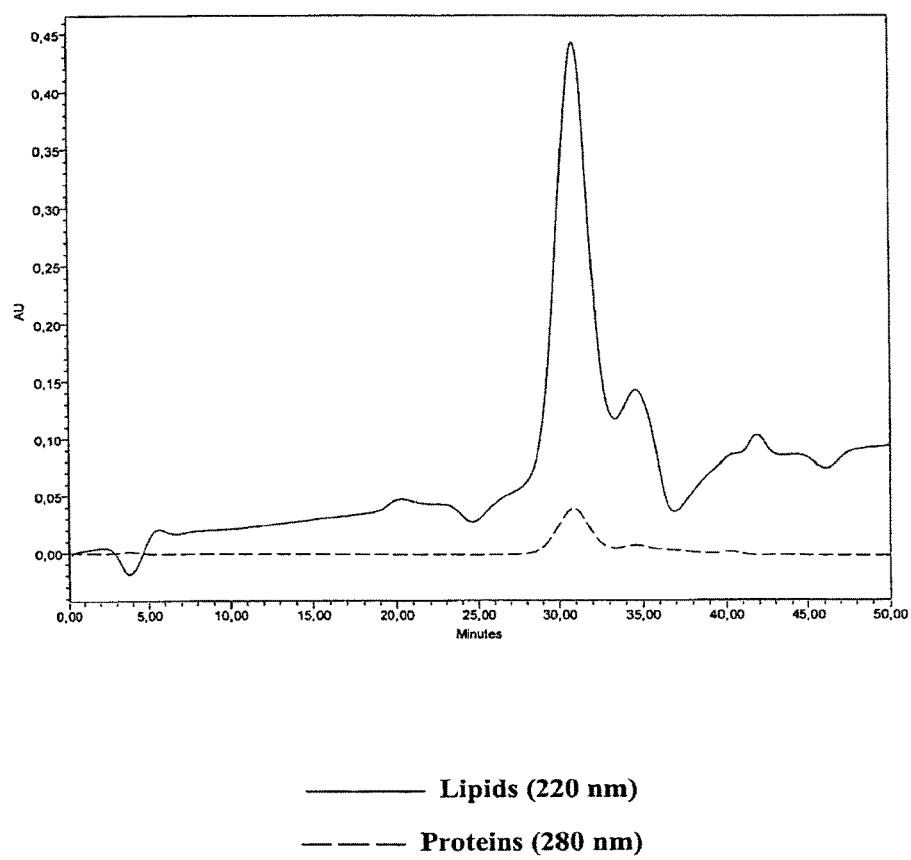
Figure 3:
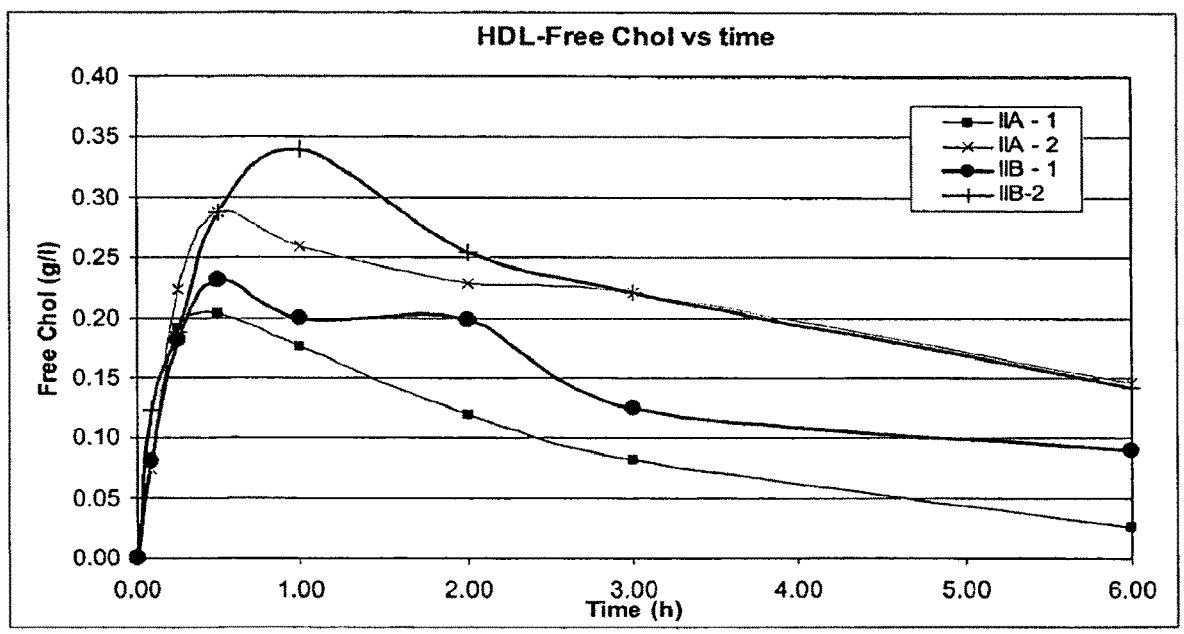
Figure 4:
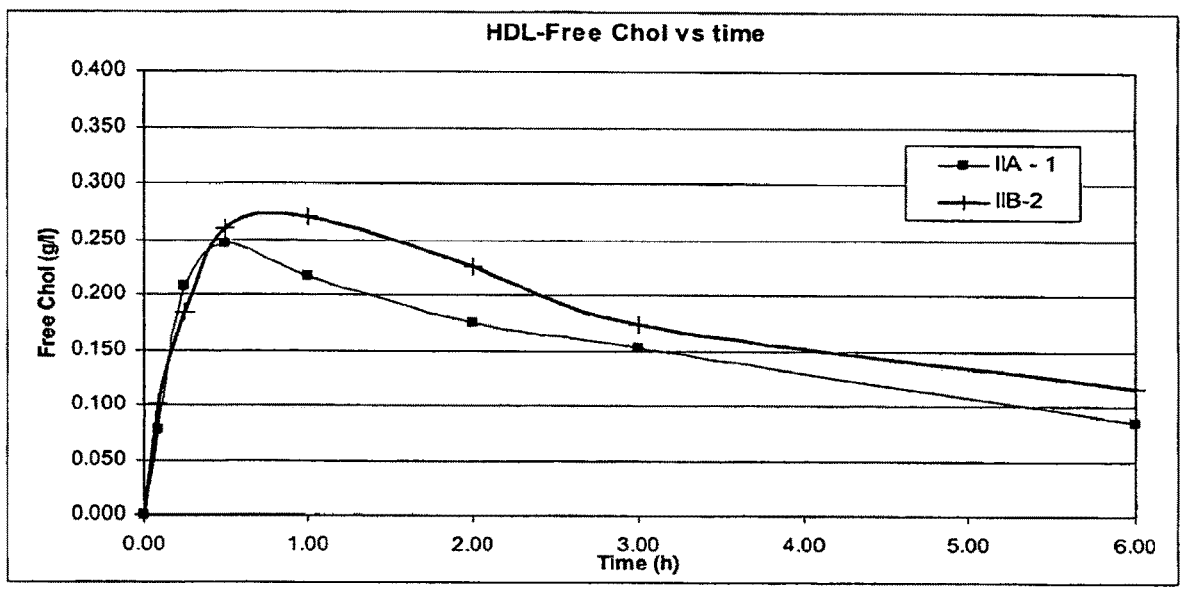

FIG. 1 provides a chromatogram of an uncharged lipoprotein complex consisting of proApo-AT (33 wt %) and sphingomyelin (67 wt %);

FIG. 2 provides a chromatogram of an embodiment of a charged lipoprotein complex consisting of proApo-AI (33 wt %), sphingomyelin (65 wt %) and phosphatidylglycerol (2 wt %);

FIG. 3 provides graphs illustrating the total amount of free cholesterol in HDL measured as a function of time in rabbits following administration of a control, uncharged lipoprotein complex (curves labeled IIA) or an embodiment of a charged lipoprotein complex as described herein (curves labeled IIB); and FIG. 4 provides a graph illustrating the averaged amount of free cholesterol in HDL measured as a function of time in rabbits administered a control, uncharged lipoprotein complex (group IIA; two animals) or an embodiment of a charged lipoprotein complex as described herein (group IIB; two animals).

6. DETAILED DESCRIPTION

The present disclosure provides charged lipoprotein complexes and compositions that are useful for, among other things, the treatment and/or prophylaxis of dyslipidemia and/or diseases, disorders and/or conditions associated with dyslipidemia. As discussed in the Summary section, the charged lipoprotein complexes comprise two major fractions, an apolipoprotein fraction and a lipid fraction, and include as a key ingredient a specified amount of one or more charged phospholipids.

The charged lipoprotein complexes can be isolated from natural sources, such has from human serum (referred to herein as "isolated charged lipoprotein complexes"), or they can be made or reconstituted from their individual components (referred to herein as "reconstituted charged lipoprotein complexes"). As will be appreciated by skilled artisans, reconstituted charged lipoprotein complexes can be advantageous in many applications, because the identities and amounts of their various components can be selectively controlled.

6.1 Apolipoproteins and Apolipoprotein Peptides

The nature of the apolipoproteins comprising the apolipoprotein fraction of the charged lipoprotein complexes is not critical for success. Virtually any apolipoprotein and/or derivative or analog thereof that provides therapeutic and/or prophylactic benefit as described herein can be included in the charged complexes. Moreover, any alpha-helical peptide or peptide analog, or any other type of molecule that "mimics" the activity of an apolipoprotein (such as, for example ApoA-I) in that it can activate LCAT or form discoidal particles when associated with lipids, can comprise the charged complexes, and is therefore included within the definition of "apolipoprotein." Examples of suitable apolipoproteins include, but are not limited to, preproapolipoprotein forms of ApoA-I, ApoA-IV, ApoA-V and ApoE; pro- and mature forms of human ApoA-I, ApoA-IV, and ApoE; and active polymorphic forms, isoforms, variants and mutants as well as truncated forms, the most common of which are ApoA-$I_M$ (ApoA-$I_M$) and ApoA-$I_P$ (ApoA-$I_P$). Apolipoproteins mutants containing cysteine residues are also known, and can also be used (see, e.g., U.S. 2003/0181372). The apolipoproteins may be in the form of monomers or dimers, which may be homodimers or heterodimers. For example, homo- and heterodimers (where feasible) of pro- and mature ApoA-I (Duverger et al., 1996, Arterioscler. Thromb. Vase. Biol. 16(12):1424-29), ApoA-$I_M$ (Franceschini et al., 1985, J. Biol. Chem. 260:1632-35), ApoA-$I_P$ (Daum et al., 1999, J. Mol. Med. 77:614-22), ApoA-II (Shelness et al., 1985, J. Biol. Chem. 260(14): 8637-46; Shelness et al., 1984, J. Biol. Chem. 259(15):9929-35), ApoA-IV (Duverger et al., 1991, Euro. J. Biochem. 201(2):373-83), ApoE (McLean et al., 1983, J. Biol. Chem. 258(14):8993-9000), ApoJ and ApoH may be used. The apolipoproteins may include residues corresponding to elements that facilitate their isolation, such as His tags, or other elements designed for other purposes, so long as the apolipoprotein retains some biological activity when included in a complex.

Such apolipoproteins can be purified from animal sources (and in particular from human sources) or produced recombinantly as is well-known in the art, see, e.g., Chung et al., 1980, J. Lipid Res. 21(3):284-91; Cheung et al., 1987, J. Lipid Res. 28(8):913-29. See also U.S. Pat. Nos. 5,059,528, 5,128,318, 6,617,134, and U.S. Publication Nos. 20002/0156007, 2004/0067873, 2004/0077541, and 2004/0266660.

Non-limiting examples of peptides and peptide analogs that correspond to apolipoproteins, as well as agonists that mimic the activity of ApoA-I, ApoA-$I_M$, ApoA-II, ApoA-IV, and ApoE, that are suitable for use as apolipoproteins in the charged complexes and compositions described herein are disclosed in U.S. Pat. Nos. 6,004,925, 6,037,323 and 6,046,166 (issued to Dasseux et al.), U.S. Pat. No. 5,840,688 (issued to Tso), U.S. publications 2004/0266671, 2004/0254120, 2003/0171277 and 2003/0045460 (to Fogelman), and U.S. publication 2003/0087819 (to Biclicki), the disclosures of which are incorporated herein by reference in their entireties. These peptides and peptide analogues can be composed of L-amino acid or D-amino acids or mixture of L- and D-amino acids. They may also include one or more non-peptide or amide linkages, such as one or more well-known peptide/amide isosteres. Such "peptide and/or peptide mimetic" apolipoproteins can be synthesized or manufactured using any technique for peptide synthesis known in the art, including, e.g., the techniques described in U.S. Pat. Nos. 6,004,925, 6,037,323 and 6,046,166.

The charged complexes may include a single type of apolipoprotein, or mixtures of two or more different apolipoproteins, which may be derived from the same or different species. Although not required, the charged lipoprotein complexes will preferably comprise apolipoproteins that are derived from, or correspond in amino acid sequence to, the animal species being treated, in order to avoid inducing an immune response to the therapy. The use of peptide mimetic apolipoproteins may also reduce or avoid an immune response.

6.2 Phospholipids

The lipid fraction of the charged complexes and compositions includes two types of phospholipids: a neutral phospholipid and a charged phospholipid. As used herein, "neutral phospholipids" are phospholipids that have a net charge of about zero at physiological pH. In many embodiments, neutral phospholipids are zwitterions, although other types of net neutral phospholipids are known and may be used. The neutral phospholipid comprises one or both of the lecithin and/or SM, and may optionally include other neutral phospholipids. In some embodiments, the neutral phospholipid comprises lecithin, but not SM. In other embodiments, the neutral phospholipid comprises SM, but not lecithin. In still other embodiments, the neutral phospholipid comprises both lecithin and SM. All of these specific exemplary embodiments can include neutral phospholipids in addition to the lecithin and/or SM, but in many embodiments do not include such additional neutral phospholipids.

The identity of the SM used is not critical for success. Thus, as used herein, the expression "SM" includes not only sphingomyelins derived from natural sources, but also analogs and derivatives of naturally occurring SMs that are impervious to hydrolysis by LCAT, as is naturally occurring SM. SM is a phospholipid very similar in structure to lecithin, but, unlike lecithin, it does not have a glycerol backbone, and hence does not have ester linkages attaching the acyl chains. Rather, SM has a ceramide backbone, with amide linkages connecting the acyl chains. SM is not a substrate for LCAT, and generally cannot be hydrolyzed by it. It can act, however, as an inhibitor of LCAT or can decrease LCAT activity by diluting the concentration of the substrate phospholipid. Because SM is not hydrolyzed, it remains in the circulation longer. It is expected that this feature will permit charged lipoprotein complexes that include SM to have a longer duration of pharmacological effect (mobilization of cholesterol) and to pick up more lipids, in particular cholesterol, than apolipoprotein complexes that do not include SM (see, e.g., the apolipoprotein complexes described in US Publication No. 2004/0067873, the disclosure of which is incorporated herein by reference in its entirety). This effect may result in less frequent or smaller doses being necessary for treatment than are required for lipoprotein complexes that do not include SM.

The SM may be derived from virtually any source. For example, the SM may be obtained from milk, egg or brain. SM analogues or derivatives may also be used. Non-limiting examples of useful SM analogues and derivatives include, but are not limited to, palmitoylsphingomyelin, stearoylsphingomyelin, D-eiythro-N-16:0-sphingomyelin and its dihydro isomer, D-erythro-N-16:0-dihydro-sphingomyelin.

Sphingomyelins isolated from natural sources may be artificially enriched in one particular saturated or unsaturated acyl chain. For example, milk sphingomyelin (Avanti Phospholipid, Alabaster, Ala.) is characterized by long saturated acyl chains (i.e., acylchains having 20 or more carbon atoms). In contrast, egg sphingomyelin is characterized by short saturated acyl chains (i.e., acyl chains having fewer than 20 carbon atoms). For example, whereas only about 20% of milk sphingomyelin comprises C16:0 (16 carbon, saturated) acyl chains, about 80% of egg sphingomyelin comprises C16:0 acyl chains. Using solvent extraction, the composition of milk sphingomyelin can be enriched to have an acyl chain composition comparable to that of egg sphingomyelin, or vice versa.

The SM may be semi-synthetic such that it has particular acyl chains. For example, milk sphingomyelin can be first purified from milk, then one particular acyl chain, e.g., the C16:0 acyl chain, can be cleaved and replaced by another acyl chain. The SM can also be entirely synthesized, by e.g., large-scale synthesis. See, e.g., Dong et al, U.S. Pat. No. 5,220,043, entitled Synthesis of D-erythro-sphingomyelins, issued Jun. 15, 1993; Weis, 1999, Chem. Phys. Lipids 102(1-2):3-12.

The lengths and saturation levels of the acyl chains comprising a semi-synthetic or a synthetic SM can be selectively varied. The acyl chains can be saturated or unsaturated, and can contain from about 6 to about 24 carbon atoms. Each chain may contain the same number of carbon atoms or, alternatively each chain may contain different numbers of carbon atoms. In some embodiments, the semi-synthetic or synthetic SM comprises mixed acyl chains such that one chain is saturated and one chain is unsaturated. In such mixed acyl chain SMs, the chain lengths can be the same or different. In other embodiments, the acyl chains of the semi-synthetic or synthetic SM are either both saturated or both unsaturated. Again, the chains may contain the same or different numbers of carbon atoms. In some embodiments, both acyl chains comprising the semi-synthetic or synthetic SM are identical. In a specific embodiment, the chains correspond to the acyl chains of a naturally-occurring fatty acid, such as for example oleic, palmitic or stearic acid. In another specific embodiment, both acyl chains are saturated and contain from 6 to 24 carbon atoms. Non-limiting examples of acyl chains present in commonly occurring fatty acids that can be included in semi-synthetic and synthetic SMs are provided in Table 1, below:

TABLE 1

| Length:Number of Unsaturations | Common Name |
|---|---|
| 14:0 | myristic acid |
| 16:0 | palmitic acid |
| 18:0 | stearic acid |
| 18:1 cis$\Delta^9$ | oleic acid |
| 18:2 cis$\Delta^{9, 12}$ | linoleic acid |
| 18:3 cis$\Delta^{9, 12, 15}$ | linonenic acid |
| 20:4 cis$\Delta^{5, 8, 11, 14}$ | arachidonic acid |
| 20:5 cis$\Delta^{5, 8, 11, 14, 17}$ | eicosapentaenoic acid (an omega-3 fatty acid) |

Like the SM, the identity of the lecithin used is not critical for success. Also, like the SM, the lecithin can be derived or isolated from natural sources, or it can be obtained synthetically. Examples of suitable lecithins isolated from natural sources include, but are not limited to, egg phosphatidylcholine and soybean phosphatidylcholine. Additional non-limiting examples of suitable lecithins include, dipalmitoylphosphatidylcholine, dimyristoylphosphatidylcholine, distearoylphosphatidylcholine 1-myristoyl-2-paimitoylphosphatidylcholine, 1-paimitoyl-2-myristoylphosphatidylcholine, 1-palmitoyl-2-stearoylphosphatidylcholine, 1-stearoyl-2-palmitoylphosphatidylcholine, 1-palmitoyl-2-oleoylphosphatidylcholine, 1-oleoyl-2-palmitylphosphatidylcholine, dioleoylphosphatidylcholine and the ether derivatives or analogs thereof.

Like the SM, lecithins derived or isolated from natural sources can be enriched to include specified acyl chains. In embodiments employing semi-synthetic or synthetic lecithins, the identity(ies) of the acyl chains can be selectively varied, as discussed above in connection with SM. In some embodiments of the charged complexes described herein, both acyl chains on the lecithin are identical. In some embodiments of charged lipoprotein complexes that include both SM and lecithin, the acyl chains of the SM and lecithin are all identical. In a specific embodiment, the acyl chains correspond to the acyl chains of myristitic, palmitic, oleic or stearic acid.

The lipid fraction also includes a charged phospholipid. As used herein, "charged phospholipids" are phospholipids that have a net charge at physiological pH. The charged phospholipid may comprise a single type of charged phospholipid, or a mixture of two or more different, typically like-charged, phospholipids. In some embodiments, the charged phospholipids are negatively charged glycerophospholipids. The identity(ies) of the charged phospholipids(s) are not critical for success. Specific examples of suitable negatively charged phospholipids include, but are not limited to, phosphatidylgycerol, phospatidylinositol, phosphatidylserine, phosphatidylglycerol and phosphatidic acid. In some embodiments, the negatively charged phospholipid comprises one or more of phosphatidylinositol, phosphatidylserine, phosphatidylglycerol and/or phosphatidic acid.

Like the SM and lecithin, the negatively charged phospholipids can be derived from natural sources or prepared by chemical synthesis. In embodiments employing synthetic negatively charged phospholipids, the identities of the acyl chains can be selectively varied, as discussed above in connection with SM. In some embodiments of the charged lipoprotein complexes described herein, both acyl chains on the negatively charged phospholipids are identical. In some embodiments of the ternary and quaternary charged lipoprotein complexes described herein, the acyl chains on the SM, the lecithin and the negatively charged phospholipids are all identical. In a specific embodiment, the charged phospholipid(s), and/or SM all have C16:0 or C16:1 acyl chains. In another specific embodiment, the acyl chains of the charged phospholipid(s), lecithin and/or SM correspond to the acyl chain of palmitic acid. In yet another specific embodiment, the acyl chains of the charged phospholipid(s), lecithin and/or SM correspond to the acyl chain of oleic acid.

The total amount of negatively charged phospholipids(s) comprising the charged complexes can vary. Typically, the lipid fraction will comprise from about 0.2 to 10 wt % negatively charged phospholipids(s). In some embodiments, the lipid fraction comprises about 0.2 to 1 wt %, 02. to 2 wt %, 02. to 3 wt %, 0.2 to 4 wt %, 0.2 to 5 wt %, 0.2 to 6 wt %, 0.2 to 7 wt %, 0.2 to 8 wt % or 0.2 to 9 wt % total negatively charged phospholipids(s). In some embodiments, the lipid fraction comprises about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 wt % total negatively charged phospholipid(s), and/or a range including any of these values as endpoints. In some embodiments, the lipid fraction comprises from about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 wt % total negatively charged phospholipid(s) up to about 4, 5, 6, 7, 8, 9 or 10 wt % total negatively charged phospholipid(s).

It is expected that the inclusion of negatively charged phospholipids in the charged lipoprotein complexes described herein will provide the complexes with greater stability (in solution) and longer product shelf-life compared to conventional complexes. In addition, the use of negatively charged phospholipids is expected to minimize particle aggregation (e.g., by charge repulsion), thereby effectively increasing the number of available complexes present in a given dosage regime, and aid the targeting of the complex for recognition by the liver and not the kidney.

Some apolipoproteins exchange in vivo from one lipoprotein complex to another (this is true for apolipoprotein ApoA-I). During the course of such exchange, the apolipoprotein typically carries with it one or more phospholipid molecules. Owing to this property, it is expected that the charged lipoprotein complexes described herein will "seed" negatively charged phospholipids to endogenous HDL, thereby transforming them into alpha particles that are more resistant to elimination by the kidneys. Thus, it is expected that administration of the charged lipoprotein complexes and compositions described herein will increase serum levels of HDL, and/or alter endogenous HDL half-life as well as endogenous HDL metabolism. It is expected that this will result in alteration of cholesterol metabolism and reverse lipid transport.

In addition to the neutral and charged phospholipids(s), the lipid fraction may optionally include additional lipids. Virtually any type of lipids may be used, including, but not limited to, lysophospholipids, galactocerebroside, gangliosides, cerebrosides, glycerides, triglycerides, and cholesterol and its derivatives.

When included, such optional lipids will typically comprise less than about 50 wt % of the lipid fraction, although in some instances more optional lipids could be included. In some embodiments, the lipid fraction of the charged lipoprotein complexes does not include optional lipids.

As indicated in the Summary section, the total amount of neutral phospholipid(s) comprising the lipid fraction of the charged lipoprotein complexes can vary, and will typically range from about 50 to 99.8 wt %, depending upon the total amount of charged phospholipid(s) included, and whether any optional lipids are included. Specific embodiments in which optional lipids are not included will typically comprise about 90 to 99.8 wt % total neutral phospholipid(s). Suitable lecithin:SM molar ratios for lipid fractions including both lecithin and SM are described in the Summary section.

In a specific embodiment, the charged lipoprotein complex is a ternary complex in which the lipid fraction consists essentially of about 90 to 99.8 wt % SM and about 0.2 to 10 wt % negatively charged phospholipid, for example, about 0.2-1 wt %, 0.2-2 wt %, 0.2-3 wt %, 0.2-4 wt %, 0.2-5 wt %, 0.2-6 wt %, 0.2-7 wt %, 0.2-8 wt %, 0.2-9 wt %, or 0.2-10 wt % total negatively charged phospholipid(s). In another specific embodiment, the charged lipoprotein complex is a ternary complex in which the lipid fraction consists essentially of about 90 to 99.8 wt % lecithin and about 0.2 to 10 wt % negatively charged phospholipid, for example, about 0.2-1 wt %, 0.2-2 wt %, 0.2-3 wt %, 0.2-4 wt %, 0.2-5 wt %, 0.2-6 wt %, 0.2-7 wt %, 0.2-8 wt %, 0.2-9 wt % or 0.2-10 wt % total negatively charged phospholipid(s).

In still another specific embodiment, the charged lipoprotein complex is a quaternary complex in which the lipid fraction consists essentially of about 9.8 to 90 wt % SM, about 9.8 to 90 wt % lecithin and about 0.2-10 wt % negatively charged phospholipid, for example, from about 0.2-1 wt %, 0.2-2 wt %, 0.2-3 wt %, 0.2-4 wt %, 0.2-5 wt %, 0.2-6 wt %, 0.2-7 wt %, 0.2-8 wt %, 0.2-9 wt %, to 0.2-10 wt % total negatively charged phospholipid(s).

The complexes may also optionally include other proteins, such as, for example, paraoxonase (PON) or LCAT, antioxidants, cyclodextrins and/or other materials that help trap cholesterol in the core or the surface of the complex. The complex can optionally be pegylated (e.g., covered with polyethylene glycol or other polymer) to increase circulation half-life.

As will be recognized by skilled artisans, the molar ratio of the lipid fraction to the apolipoprotein fraction of the charged lipoprotein complexes described herein can vary, and will depend upon, among other factors, the identity(ies) of the apolipoprotein comprising the apolipoprotein fraction, the identities and quantities of the charged phospholipids comprising the lipid fraction, and the desired size of the charged lipoprotein complex. Because the biological activity of apolipoproteins such as ApoA-I are thought to be mediated by the amphipathic helices comprising the apolipoprotein, it is convenient to express the apolipoprotein fraction of the lipid:apolipoprotein molar ratio using ApoA-I protein equivalents. It is generally accepted that ApoA-I contains 6-10 amphipathic helices, depending upon the method used to calculate the helices. Other apolipoproteins can be expressed in terms of ApoA-I equivalents based upon the number of amphipathic helices they contain. For example, ApoA-I$_M$, which typically exists as a disulfide-bridged dimer, can be expressed as 2 ApoA-I equivalents, because each molecule of ApoA-I$_M$ contains twice as many amphipathic helices as a molecule of ApoA-I. Conversely, a peptide apolipoprotein that contains a single amphipathic helix can be expressed as a 1/10-1/6 ApoA-I equivalent, because each molecule contains 1/10-1/6 as many amphipathic helices as a molecule of ApoA-I. In general, the lipid:ApoA-I equivalent molar ratio of the charged lipoprotein complexes (defined herein as "$R_i$") will range from about 2:1 to 100:1. In some embodiments, the $R_i$ is about 50:1. Ratios in weight can be obtained using a MW of approximately 650-800 for phospholipids.

The size of the charged lipoprotein complex can be controlled by varying the $R_i$. That is, the smaller the $R_i$, the smaller the disk. For example, large discoidal disks will typically have an $R_i$ in the range of about 200:1 to 100:1, whereas small discoidal disks will typically have an $R_i$ in the range of about 100:1 to 30:1.

In some specific embodiments, the charged lipoprotein complexes are large discoidal disks that contain 2-4 ApoA-I equivalents (e.g., 2-4 molecules of ApoA-I, 1-2 molecules of ApoA-I$_M$ dimer or 6-10 single-helix peptide molecules), 1 molecule of charged phospholipid and 400 molecules of total neutral phospholipid. In other specific embodiments, the charged lipoprotein complexes are small discoidal disks that contain 2-4 ApoA-I equivalents, 1 molecule of charged phospholipid and 200 molecules of total neutral phospholipids.

The various apolipoprotein and/or phospholipids molecules comprising the charged lipoprotein complexes may be labeled with any art-known detectable marker, including stable isotopes (e.g., $^{13}C$, $^{15}N$, $^{2}H$, etc.); radioactive isotopes (e.g., $^{14}C$, $^{3}H$, $^{125}I$, etc.); fluoro pores; chemiluminescers; or enzymatic markers.

6.3 Methods of Making Charged Lipoprotein Complexes

The charged lipoprotein complexes described herein can be prepared in a variety of forms, including, but not limited to vesicles, liposomes, proteoliposomes, micelles, and discoidal particles. A variety of methods well known to those skilled in the art can be used to prepare the charged lipoprotein complexes. A number of available techniques for preparing liposomes or proteoliposomes may be used. For example, apolipoprotein can be co-sonicated (using a bath or probe sonicator) with the appropriate phospholipids to form complexes. Alternatively, apolipoprotein can be combined with preformed lipid vesicles resulting in the spontaneous formation of charged lipoprotein complexes. The charged lipoprotein complexes can also be formed by a detergent dialysis method; e.g., a mixture of apolipoprotein, charged phospholipid(s) SM and/or lecithin and a detergent such as cholate is dialyzed to remove the detergent and reconstituted to form charged lipoprotein complexes (see, e.g., Jonas et al., 1986, Methods in Enzymol. 128:553-82), or by using an extruder device or by homogenization.

In some embodiments, charged lipoprotein complexes can be prepared by the cholate dispersion method described in Example 1 of U.S. publication 2004/0067873, the disclosure of which is incorporated herein by reference. Briefly, dry lipid is hydrated in NaHCO$_3$ buffer, then vortexed and sonicated until all lipid is dispersed. Cholate solution is added, the mixture is incubated for 30 minutes, with periodic vortexing and sonicating, until it turns clear, indicating that the lipid cholate micelles are formed. ProApoA-I in NaHCO$_3$ buffer is added, and the solution incubated for 1 hour at approximately 37° C.-50° C. The ratio of lipid:proApoA-I in the solution can be from 1:1 to 200:1 (mole/mole), but in some embodiments, the ratio is about 2:1 weight of lipid to weight of protein (wt/wt).

Cholate can be removed by methods well known in the art. For example cholate can be removed by dialysis, ultrafiltration or by removal of cholate molecules by adsorption absorption onto an affinity bead or resin. In one embodiment, the affinity beads, e.g., BIO-BEADS® (Bio-Rad Laboratories) are added to the preparation of charged lipoprotein complexes and cholate to adsorb the cholate. In another embodiment, the preparation, e.g., a micellar preparation of the charged lipoprotein complexes and cholate, is passed over a column packed with affinity beads.

In a specific embodiment, cholate is removed from a preparation of charged lipoprotein complexes by loading the preparation onto BIO-BEADS® within a syringe. The syringe is then sealed with barrier film and incubated with rocking at 4° C. overnight. Before use, the cholate is remove by injecting the solution through BIO-BEADS®, where it is adsorbed by the beads.

The charged lipoprotein complexes are expected to have an increased half-life in the circulation when the complexes have a similar size and density to HDL, especially to the HDLs in the pre-beta-1 or pre-beta-2 HDL populations. Stable preparations having a long shelf life may be made by lyophilization. For example, the co-lyophilization procedure described below provides a stable formulation and ease of formulation/particle preparation process. Co-lyophilization methods are also described in U.S. Pat. No. 6,287,590 (entitled Peptide/lipid complex formation by co-lyophilization, by Dasseux, issued Sep. 11, 2001), which is incorporated herein by reference in its entirety. The lyophilized charged lipoprotein complexes can be used to prepare bulk supplies for pharmaceutical reformulation, or to prepare individual aliquots or dosage units that can be reconstituted by rehydration with sterile water or an appropriate buffered solution prior to administration to a subject.

U.S. Pat. Nos. 6,004,925, 6,037,323, 6,046,166 and 6,287,590 (incorporated herein by reference in their entireties) disclose a simple method for preparing charged lipoprotein complexes that have characteristics similar to HDL. This method, which involves co-lyophilization of apolipoprotein and lipid solutions in organic solvent (or solvent mixtures) and formation of charged lipoprotein complexes during hydration of the lyophilized powder, has the following advantages: (1) the method requires very few steps; (2) the method uses inexpensive solvent(s); (3) most or all of the included ingredients are used to form the designed complexes, thus avoiding waste of starting material that is common to the other methods; (4) lyophilized complexes are formed that are very stable during storage such that the resulting complexes may be reconstituted immediately before use; (5) the resulting complexes usually need not be further purified after formation and before use; (6) toxic compounds, including detergents such as cholate, are avoided; and (7) the production method can be easily scaled up and is suitable for GMP manufacture (i.e., in an endotoxin-free environment).

In some embodiments, co-lyophilization methods commonly known in the art are used to prepare charged lipoprotein complexes. Briefly, the co-lyophilization steps include solubilizing the apolipoprotein ("Apo") and phospholipids together in an organic solvent or solvent mixture, or solubilizing the Apo and phospholipids separately and mixing them together. The desirable characteristics of solvent or solvent mixture are: (i) a medium relative polarity to be able to dissolve hydrophobic lipids and amphipatic protein, (ii) solvents should be class 2 or 3 solvent according to FDA solvent guidelines (Federal. Register, volume 62, No. 247) to avoid potential toxicity associated with the residual organic solvent, (iii) low boiling point to assure ease of solvent removal during lyophilization, (iv) high melting point to provide for faster freezing, higher temperatures of condenser and, hence less ware of freeze-dryer. In a preferred embodiment, glacial acetic acid is used. Combinations of e.g., methanol, glacial acetic acid, xylene, or cyclohexane may also be used.

The Apo/lipid solution is then lyophilized to obtain homogeneous Apo/lipid powder. The lyophilization conditions can be optimized to obtain fast evaporation of solvent with minimal amount of residual solvent in the lyophilized Apo/lipid powder. The selection of freeze-drying conditions can be determined by the skilled artisan, and depends on the nature or solvent, type and dimensions of the receptacle, e.g., vial, holding solution, fill volume, and characteristics of freeze-dryer used. The concentration of lipid/Apo solution prior to the lyophilization, for organic solvent removal and successful formation of complexes, can range from 10 to 50 mg/ml concentration of ApoA-I equivalent and from 20 to 100 mg/ml concentrations of lipid.

The Apo-lipid complexes form spontaneously after hydration of Apo-lipid lyophilized powder with an aqueous media of appropriate pH and osmolality. In some embodiments, the media may also contain stabilizers such as sucrose, trehalose, glycerin and others. In some embodiments, the solution must be heated several times above transition temperature for lipids for complexes to form. The molar ratio of lipid to protein for successful formation of charged lipoprotein complexes can be from 2:1 to 200:1 (expressed in ApoA-I equivalents) and is preferably about 2:1 weight of lipid to weight of protein (wt/wt). Powder is hydrated to obtain final complex concentration of about 5-30 mg/ml expressed, in ApoA-I protein equivalents.

In some embodiments, Apo powder is obtained by freeze-drying Apo solution in $NH_4CO_3$ aqueous solution. A homogeneous solution of Apo and lipids is formed by dissolving their powders and Apo in glacial acetic acid. The solution is then lyophilized, and HDL-like charged lipoprotein complexes are formed by hydration of lyophilized powder with aqueous media.

In some embodiments, homogenization is used to prepare Apo-lipid complexes. This method may be used to prepare Apo soybean-PC complexes and is routinely used for formulation of ApoA-I$_M$-POPC complexes. Homogenization can be easily adapted for formation of charged lipoprotein complexes. Briefly, this method comprises forming a suspension of lipids in aqueous solution of Apo by Ultraturex™, and homogenization of formed lipid-protein suspension using high-pressure homogenizer until suspension becomes clear-opalescent solution and complexes are formed. Elevated temperatures above lipid transition are used during homogenization. Solution is homogenized for extended period of time 1-14 hours and elevated pressure.

In some embodiments, charged lipoprotein complexes can be formed by co-lyophilization of phospholipid with peptide or protein solutions or suspensions. The homogeneous solution of peptide/protein, charged phospholipids, SM and/or lecithin (plus any other phospholipid of choice) in an organic solvent or organic solvent mixture can be lyophilized, and charged lipoprotein complexes can be formed spontaneously by hydration of the lyophilized powder with an aqueous buffer. Examples of organic solvents or their mixtures are include, but are not limited to, acetic acid, acetic acid and xylene, acetic acid and cyclohexane, and methanol and xylene.

A suitable proportion of protein (peptide) to lipid can be determined empirically so that the resulting complexes possess the appropriate physical and chemical properties; i.e., usually (but not necessarily) similar in size to HDL. The resulting mixture of Apo and lipid in solvent is frozen and lyophilized to dryness. Sometimes an additional solvent must be added to the mixture to facilitate lyophilization. It is expected that this lyophilized product will be able to be stored for long periods and will remain stable.

The lyophilized product can be reconstituted in order to obtain a solution or suspension of the charged lipoprotein complex. To this end, the lyophilized powder is rehydrated with an aqueous solution to a suitable volume (typically 5-20 mg charged lipoprotein complex/ml) which is convenient for e.g., intravenous injection. In a preferred embodiment the lyophilized powder is rehydrated with phosphate buffered saline, saline bicarbonate, or a physiological saline solution. The mixture may be agitated or vortexed to facilitate rehydration. In general, the reconstitution step should be conducted at a temperature equal to or greater than the phase transition temperature of the lipid component of the complexes. Within minutes of reconstitution, a clear preparation of reconstituted charged lipoprotein complexes should result.

Other methods include spray-drying, where solutions are sprayed and solvent evaporated (either at elevated temperatures or at reduced pressure). Lipids and apolipoproteins could be solubilized in the same solvent or in different solvents. Powder filling can then be used to fill vials.

Lyophilized powder from apolipoproteins and lipids could also be mixed mechanically. Homogeneous powder containing the apolipoprotein and lipids could then be hydrated to form spontaneously complexes of the appropriate size and the appropriate lipid:apolipoprotein molar ratio.

An aliquot of the resulting reconstituted preparation can be characterized to confirm that the complexes in the preparation have the desired size distribution; e.g., the size distribution of HDL. Characterization of the reconstituted preparation can be performed using any method known in the art, including, but not limited to, size exclusion filtration, gel filtration, column filtration, gel permeation chromatography, and non-denaturating gel electrophoresis.

For example, after hydration of lyophilized charged lipoprotein powder or at the end of homogenization or cholate dialysis formed Apo-lipid HDL-like particles are characterized with respect to their size, concentration, final pH and osmolality of resulting solution, in some instances, integrity of lipid and/or apolipoprotein are characterized. The size of the resulting charged lipoprotein particles is determinative of their efficacy, therefore this measurement is typically included for characterization of the particles.

In some embodiments, gel permeation chromatography (GPC), e.g., a high pressure liquid chromatography system equipped with a 1×30 cm Superdex™ column (Pharmacia Biotech) and UV-detector may be used. Complexes are eluted with bicarbonate buffered saline comprised of 140 mM NaCl and 20 mM sodium bicarbonate delivered with 0.5 ml/min flow rate. A typical amount of complex injected is 0.1 to 1 mg based on protein weight. The complexes can be monitored by absorbance at 280 nm.

Protein and lipid concentration of charged lipoprotein particles solution can be measured by any method known in the art, including, but not limited to, protein and phospholipid assays as well as by chromatographic methods such as HPLC, gel filtration chromatography, GC coupled with various detectors including mass spectrometry, UV or diode-assay, fluorescent, elastic light scattering and others. The integrity of lipid and proteins can be also determined by the same chromatographic techniques as well as peptide mapping, SDS-page gel, N- and C-terminal sequencing for proteins and standard assays to determine lipid oxidation for lipids.

The homogeneity and/or stability of the charged lipoprotein complexes or composition described herein can be measured by any method known in the art, including, but not limited to, chromatographic methods such as gel filtration chromatography. For example, in some embodiments a single peak or a limited number of peaks can be associated with a stable complex. The stability of the complexes can be determined by monitoring the appearance of new of peaks over time. The appearance of new peaks is a sign of reorganization among the complexes due to the instability of the particles.

The optimum ratio of phospholipids to apolipoprotein(s) in the charged complexes can be determined using any number of functional assays known in the art, including, but not limited to, gel electrophoresis mobility assay, size exclusion chromatography, interaction with HDL receptors, recognition by ATP-binding cassette transporter (ABCA1), uptake by the liver, and pharmacokinetics/pharmacodynamics. For example, gel electrophoresis mobility assays can be used to determine the optimum ratio of phospholipids to apolipoproteins in the charged complexes. The charged complexes described herein should exhibit an electrophoretic mobility that is similar to natural pre-beta-HDL or alpha-HDL particles. Thus, in some embodiments, natural pre-beta-HDL or alpha-HDL particles can be used as standard for determining the mobility of the charged complexes.

As another example, size exclusion chromatography can be used to determine the size of the charged complexes described herein as compared to natural pre-beta-HDL particles. Natural pre-beta-HDL particles generally are not larger than 10-12 nm, and discoidal particles are usually around 7-10 nm.

As another example, HDL receptors can be used in a functional assay to identify which complex is closest to natural pre-beta-HDL particles, or to identify which complex is the most effective in removing and/or mobilizing cholesterol or lipids from a cell. In one assay, the complexes can be tested for their ability to bind ABCA-1 receptors. Such an assay can differentiate ABCA-1 dependent on independent removal of cholesterol. Even though ApoA-I is considered the best ligands for such an assay, complexes such as small micellar or small discoidal particles are also potent ABCA-I ligands. ABCA-1 binding assays that can be used are described in Brewer et al., 2004, Arterioscler. Thromb. Vase. Biol. 24:1755-1760).

As another example, ABCA1 expressing cells are known to recognize free ApoA-I and to a lesser extent, natural pre-beta-HDL particles (Brewer et al., 2004, Arteriosclar. Thromb. Vase. Biol. 24:1755-1760. In these embodiments, recognition of ABCA1 cells of natural pre-beta-HDL particles can be compared to any one of the charged complexes described herein to identify the complex that most closely resembles natural pre-beta-HDL particles.

A relatively simple approach for identifying charged complexes that most closely resemble natural pre-beta-HDL particles is to perfuse livers with a solution containing the reconstituted charged complexes and measure the amount that is taken up by the liver.

In some embodiments, the pharmacokinetics/pharmacodynamics (PK/PD) of the charged complexes can be measured following a single injection in rabbits. In these embodiments, the concentration of ApoA-I is used as a marker of the kinetics. The pharmacodynamics can be measured as the amount of cholesterol mobilized above baseline after a single injection, as well s the amount of cholesterol in the HDL fraction. PK and PD depend on the nature of the phospholipids, the composition of the phospholipids, the lipid:apolipoprotein molar ratio and the phospholipid concentration of the complex. For example, dipalmitoylphosphatidylcholine (DPPC)/ApoA-I complexes have a longer half-live than egg phosphatidylcholine (EPC)/ApoA-I complexes. Sphingomyelin/ApoA-I complexes have a longer half-life than EPC/ApoA-I complexes. The half-life of human ApoA-I in humans is approximately 5 to 6 days.

In another embodiment, the pharmacodynamics of the charged complex can be measured by following the rate of cholesterol esterification in the HDL fraction over time. LCAT is the only enzyme responsible for cholesterol esterification in blood. The rate of cholesterol esterification is a good parameter to access the quality of a particle. The LCAT acting as a molecular probe, the rate of esterification will be higher if the quaternary complex is recognized by the LCAT. This means that the surface is ideal, the charge is ideal, the morphology is ideal and the two substrates (LCAT first hydrolyze an acyl chain from a phospholipids (esterase activity) and then esterify the free OH from the cholesterol (esterase activity) to form a cholesteryl ester) are accessible and in the right concentrations. Also, it means that the particle is well dimensioned and composed to solubilize and trap the products of the reaction: the lysophospholipid and the cholesteryl ester otherwise the reaction would stop.

6.4 Pharmaceutical Compositions

The pharmaceutical compositions contemplated by the disclosure comprise charged lipoprotein complexes as the active ingredient in a pharmaceutically acceptable carrier suitable for administration and delivery in vivo. Since peptides may comprise acidic and/or basic termini and/or side chains, peptide mimetic apolipoproteins can be included in the compositions in either the form of free acids or bases, or in the form of pharmaceutically acceptable salts. Modified proteins such as amidated, acylated, acetylated pegylated proteins, may also be used.

Injectable compositions include sterile suspensions, solutions or emulsions of the active ingredient in aqueous or oily vehicles. The compositions can also comprise formulating agents, such as suspending, stabilizing and/or dispersing agent. The compositions for injection can be presented in unit dosage form, e.g., in ampules or in multidose containers, and can comprise added preservatives. For infusion, a composition can be supplied in an infusion bag made of material compatible with charged lipoprotein complexes, such as ethylene vinyl acetate or any other compatible material known in the art.

Alternatively, the injectable compositions can be provided in powder form for reconstitution with a suitable vehicle, including but not limited to, sterile pyrogen free water, buffer, dextrose solution, etc., before use. To this end, Apo can be lyophilized, or co-lyophilized charged lipoprotein complexes may be prepared. The stored compositions can be supplied in unit dosage forms and reconstituted prior to use in vivo.

For prolonged delivery, the active ingredient can be formulated as a depot composition, for administration by implantation; e.g., subcutaneous, intradermal, or intramuscular injection. Thus, for example, Apo-lipid complex or Apolipoprotein alone may be formulated with suitable polymeric or hydrophobic materials (e.g., as an emulsion in an acceptable oil) or in phospholipid foam or ion exchange resins.

Alternatively, transdermal delivery systems manufactured as an adhesive disc or patch that slowly releases the active ingredient for percutaneous absorption can be used. To this end, permeation enhancers can be used to facilitate transdermal penetration of the active ingredient. A particular benefit can be achieved by incorporating the charged complexes described herein into a nitroglycerin patch for use in patients with ischemic heart disease and hypercholesterolemia.

Alternatively, the delivery could be done locally or intramurally (within the vessel wall) using a catheter or perfusor (see, e.g., U.S. publication 2003/0109442).

The compositions can, if desired, be presented in a pack or dispenser device that may comprise one or more unit dosage forms comprising the active ingredient. The pack can for example comprise metal or plastic foil, such as a blister pack. The pack or dispenser device can be accompanied by instructions for administration.

6.5 Methods of Treatment

The charged lipoprotein complexes and compositions described herein can be used for virtually every purpose lipoprotein complexes have been shown to be useful. In a specific embodiment, the complexes and compositions can be used to treat or prevent dyslipidemia and/or virtually any disease, condition and/or disorder associated with dyslipidemia. As used herein, the terms "dyslipidemia" or "dyslipidemic" refer to an abnormally elevated or decreased level of lipid in the blood plasma, including, but not limited to, the altered level of lipid associated with the following conditions: coronary heart disease; coronary artery disease; cardiovascular disease, hypertension, restenosis, vascular or perivascular diseases; dyslipidemic disorders; dyslipoproteinemia; high levels of low density lipoprotein cholesterol; high levels of very low density lipoprotein cholesterol; low levels of high density lipoproteins; high levels of lipoprotein Lp(a) cholesterol; high levels of apolipoprotein B; atherosclerosis (including treatment and prevention of atherosclerosis); hyperlipidemia; hypercholesterolemia; familial hypercholesterolemia (FH); familial combined hyperlipidemia (FCH); lipoprotein lipase deficiencies, such as hypertriglyceridemia, hyperalphalipoproteinemia, and hypercholesterolemialipoprotein.

Diseases associated with dyslipidemia include, but are not limited to coronary heart disease, coronary artery disease, acute coronary syndrome, cardiovascular disease, hypertension, restenosis, vascular or perivascular diseases; dyslipidemic disorders; dyslipoproteinemia; high levels of low density lipoprotein cholesterol; high levels of very low density lipoprotein cholesterol; low levels of high density lipoproteins; high levels of lipoprotein Lp(a) cholesterol; high levels of apolipoprotein B; atherosclerosis (including treatment and prevention of atherosclerosis); hyperlipidemia; hypercholesterolemia; familial hypercholesterolemia (FH); familial combined hyperlipidemia (FCH); lipoprotein lipase deficiencies, such as hypertriglyceridemia, hypoalphalipoproteinemia, and hypercholesterolemialipoprotein.

Using the charged lipoprotein complexes and compositions described herein, a dosage of phospholipids that ranges from about 2- to 25-fold less (in ApoA-I equivalents) than the effective dosage currently known in the art is expected to be efficacious in treating or preventing the disease or in bringing about an ameliorative effect.

In one embodiment, the methods encompass a method of treating or preventing a disease associated with dyslipidemia, comprising administering to a subject a charged lipoprotein complex or composition described herein in an amount effective to achieve a serum level of free or complexed apolipoprotein for at least one day following administration that is in the range of about 10 mg/dL to 300 mg/dL higher than a baseline (initial) level prior to administration.

In another embodiment, the methods encompass a method of treating or preventing a disease associated with dyslipidemia, comprising administering to a subject a charged lipoprotein complex or composition described herein in an amount effective to achieve a circulating plasma concentrations of a HDL-cholesterol fraction for at least one day following administration that is at least about 10% higher than an initial HDL-cholesterol fraction prior to administration.

In another embodiment, the methods encompass a method of treating or preventing a disease associated with dyslipidemia, comprising administering to a subject a charged lipoprotein complex or composition described herein in an amount effective to achieve a circulating plasma concentration of a HDL-cholesterol fraction that is between 30 and 300 mg/dL between 5 minutes and 1 day after administration.

In another embodiment, the methods encompass a method of treating or preventing a disease associated with dyslipidemia, comprising administering to a subject a charged lipoprotein complex or composition described herein in an amount effective to achieve a circulating plasma concentration of cholesteryl esters that is between 30 and 300 mg/dL between 5 minutes and 1 day after administration.

In still another embodiment, the methods encompasses a method at treating or protecting a disease associated with dyslipidemia, comprising administering to a subject a charged lipoprotein complex or composition described herein in an amount effective to achieve an increase in fecal cholesterol excretion for at least one day following administration that is at least about 10% above a baseline (initial) level prior to administration.

The charged lipoprotein complexes or compositions described herein can be used alone or in combination therapy with other drugs used to treat or prevent the foregoing conditions. Such-therapies include, but are not limited to simultaneous or sequential administration of the drugs involved. For example, in the treatment of hypercholesterolemia or atherosclerosis, charged lipoprotein formulations can be administered with any one or more of the cholesterol lowering therapies currently in use; e.g., bile-acid resins, niacin, statins, inhibitors of cholesterol absorption and/or fibrates. Such a combined regimen may produce particularly beneficial therapeutic effects since each drug acts on a different target in cholesterol synthesis and transport; i.e., bile-acid resins affect cholesterol recycling, the chylomicron and LDL population; niacin primarily affects the VLDL and LDL population; the statins inhibit cholesterol synthesis, decreasing the LDL population (and perhaps increasing LDL receptor expression); whereas the charged lipoprotein complexes described herein affect RCT, increase HDL, and promote cholesterol efflux.

In another embodiment, the charged lipoprotein complexes or compositions described herein may be used in conjunction with fibrates to treat or prevent coronary heart disease; coronary artery disease; cardiovascular disease, hypertension, restenosis, vascular or perivascular diseases; dyslipidemic disorders; dyslipoproteinemia; high levels of low density lipoprotein cholesterol; high levels of very low density lipoprotein cholesterol; low levels of high density lipoproteins; high levels of lipoprotein Lp(a) cholesterol; high levels of apolipoprotein B; atherosclerosis (including treatment and prevention of atherosclerosis); hyperlipidemia; hypercholesterolemia; familial hypercholesterolemia (FH); familial combined hyperlipidemia (FCH); lipoprotein lipase deficiencies, such as hypertriglyceridemia, hypoalphalipoproteinemia, and hypercholesterolemialipoprotein. Exemplary formulations and treatment regimens are described below.

The charged lipoprotein complexes or compositions described herein can be administered by any suitable route that ensures bioavailability in the circulation. An important feature embodiments including SM is that the charged lipoprotein complexes can be administered in doses less than 1-10% of the effective dose expected to effective, for apolipoprotein (Apo) or Apo peptide administered alone, and in doses 2-25 fold less than the effective dose required for Apo-soybean PC (or Apo-egg PC or Apo-POPC) administration. Administration at doses (for intravenous injection) as low as about 40 mg to 2 g/person of apolipoprotein every 2 to 10 days is required, rather than the large amounts of apolipoprotein (20 mg/kg to 100 mg/kg per administration every 2 to 5 days, 1.4 g to 8 g per average sized human) required by currently available treatment regimens.

The charged lipoprotein complexes or compositions described herein can be administered in dosages that increase the small HDL fraction, for example, the pre-beta, pre-gamma and pre-beta-like HDL fraction, the alpha HDL fraction, the HDL3 and/or the HDL2 fraction. In some embodiments, the dosages are effective to achieve atherosclerotic plaque reduction as measured by, for example, imaging techniques such as magnetic resonance imaging (MRI) or intravascular ultrasound (IVUS). Parameters to follow by IVUS include, but are not limited to, change in percent atheroma volume from baseline and change in total atheroma volume. parameters to follow by MRI include, but are not limited to, those for IVUS and lipid composition and calcification of the plaque.

The plaque regression could be measured using the patent as its own control (time zero versus time t at the end of the last infusion, or within weeks after the last infusion, or within 3 months, 6 months, or 1 year after the start of therapy.

Administration can best be achieved by parenteral routes of administration, including intravenous (IV), intramuscular (IM), intradermal, subcutaneous (SC), and intraperitoneal (IP) injections. In certain embodiments, administration is by a perfusor, an infiltrator or a catheter. In some embodiments, the charged lipoprotein complexes are administered by injection, by a subcutaneously implantable pump or by a depot preparation, in amounts that achieve a circulating serum concentration equal to that obtained through parenteral administration. The complexes could also be absorbed in, for example, a stent or other device.

Administration can be achieved through a variety of different treatment regimens. For example, several intravenous injections can be administered periodically during a single day, with the cumulative total volume of the injections not reaching the daily toxic dose. Alternatively, one intravenous injection can be administered about every 3 to 15 days, preferably about every 5 to 10 days, and most preferably about every 10 days. In yet another alternative, an escalating dose can be administered, starting with about 1 to 5 doses at a dose between (50-200 mg) per administration, then followed by repeated doses of between 200 mg and 1 g per administration. Depending on the needs of the patient, administration can be by slow infusion with a duration of more than one hour, by rapid infusion of one hour or less, or by a single bolus injection.

In some embodiments, administration could be done as a service of injections and then stopped for 6 months to 1 year, and then another series started. Maintenance series of injections could then be administered every year or every 3 to 5 years. The series of injections could be done over a day (perfusion to maintain a specified plasma level of complexes), several days (e.g., four injections over a period of eight days) or several weeks (e.g., four injections over a period of four weeks), and then restarted after six months to a year.

Other routes of administration can be used. For example, absorption through the gastrointestinal tract can be accomplished by oral routes of administration (including but not limited to ingestion, buccal and sublingual routes) provided appropriate formulations (e.g., enteric coatings) are used to avoid or minimize degradation of the active ingredient, e.g., in the harsh environments of the oral mucosa, stomach and/or small intestine. Alternatively, administration via mucosal tissue such as vaginal and rectal modes of administration may be utilized to avoid or minimize degradation in the gastrointestinal tract. In other embodiments, the formulations of the invention can be administered transcutaneously (e.g., transdermally), or by inhalation. It will be appreciated that the preferred route may vary with the condition, age and compliance of the recipient.

The actual dose of a charged lipoprotein complex or composition described herein can vary with the route of administration.

Data obtained in animal model systems described in U.S. Pat. Nos. 6,004,925, 6,037,323 and 6,046,166 (issued to Dasseux et al., incorporated herein by reference in their entireties) show that ApoA-I peptides associate with the HDL component, and have a projected half-life in humans of about five days. Thus, in some embodiment, charged lipoprotein complexes can be administered by intravenous injection at a dose between about 0.1 g-1 g of charged lipoprotein complex per administration every 2 to 10 days per average sized human.

Toxicity and therapeutic efficacy of the various charged lipoprotein complexes can be determined using standard pharmaceutical procedures in cell culture or experimental animals for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Charged lipoprotein complexes that exhibit large therapeutic indices are preferred. Non-limiting examples of parameters that can be followed include liver function transaminases (no more than 2× normal baseline levels). This is an indication that too much cholesterol is brought to the liver and cannot assimilate such an amount. The effect on red blood cells could also be monitored, as mobilization of cholesterol from red blood cells causes them to become fragile, or affect their shape.

Patients can be treated from a few days to several weeks before a medical act (e.g., preventive treatment), or during or after a medical act. Administration can be concomitant to or contemporaneous with another invasive therapy, such as, angioplasty, carotid ablation, rotoblader or organ transplant (e.g., heart, kidney, liver, etc.).

In certain embodiments, charged lipoprotein complexes are administered to a patient whose cholesterol synthesis is controlled by a statin or a cholesterol synthesis inhibitor. In other embodiments, charged lipoprotein complexes are administered to a patient undergoing treatment with a binding resin, e.g., a semi-synthetic resin such as cholestyramine, or with a fiber, e.g., plant fiber, to trap bile salts and cholesterol, to increase bile acid excretion and lower blood cholesterol concentrations.

6.6 Other Uses

The charged lipoprotein complexes and compositions described herein can be used in assays in vitro to measure serum HDL, e.g., for diagnostic purposes. Because ApoA-I, ApoA-II and Apo peptides associate with the HDL component of serum, charged lipoprotein complexes can be used as "markers" for the HDL population, and the pre-beta1 and pre-beta2 HDL populations. Moreover, the charged lipoprotein complexes can be used as markers for the subpopulation of HDL that are effective in RCT. To this end, charged lipoprotein complexes can be added to or mixed with a patient serum sample; after an appropriate incubation time, the HDL component can be assayed by detecting the incorporated charged lipoprotein complexes. This can be accomplished using labeled charged lipoprotein complexes (e.g., radiolabels, fluorescent labels, enzyme labels, dyes, etc.), or by immunoassays using antibodies (or antibody fragments) specific for charged lipoprotein complexes.

Alternatively, labeled charged lipoprotein complexes can be used in imaging procedures (e.g., CAT scans, MRI scans) to visualize the circulatory system, or to monitor RCT, or to visualize accumulation of HDL at fatty streaks, atherosclerotic lesions, and the like, where the HDL should be active in cholesterol efflux.

Examples and data associated with the preparation and characterization of certain proApoA-I lipid complexes are described in U.S. Patent Publication No. 2004/0067873, the disclosure of which is incorporated herein by reference in its entirety.

Data obtained in an animal model system using certain proApoA-I lipid complexes are described in U.S. Patent Publication No. 2004/0067873, the disclosure of which is incorporated herein by reference in its entirety.

7. EXAMPLES

Example 1

Preparation of proApoA-I, Sphingomyelin, and Phosphatidylglycerol

The protein proApoA-I was supplied by Unite de Biotechnologie, Institut Meurice, Hte Ecole Lucia De Brouckere, 1 Avenue Emile Giyzon, B-1070 Anderlecht, Belgium in lyophilized individual 100 mL flasks containing approximately 90 mg of protein. The batch number was 20060202. The protein was kept at approximately 4° C. until use. Before lyophylization, the content of proApoA-I was 3.225 mg/mL with an urea content about 0.011 mg/mL. A solution of proApoA-I was made by dissolving approximately 630 mg of proApoA-I in 25.6 mL of acetic acid/water 5%. The final concentration of the solution was 25 mg/mL.

Sphingomyelin from egg (Coatsome® NM-10) was supplied by NOF Corporation, 1-56, Oohama-Cho, Amagasaki-Shi, 660-0095, Japan. The batch number was 0502ES1. Sphingomyelin was kept at approximately −20° C. until use. The purity of sphingomyelin was 99.1%. A solution of sphingomyelin was made by dissolving 799.4 mg of purified sphingomyelin in 16 mL of acetic acid/water 5% to yield a final concentration of 50 mg/mL.

1,2-dipalmitoyl-SN-glycero-3-phopsphatidyl glycerol as sodium salt (DPPG-Na, Coatsome® MG-6060LS) was supplied by NOF Corporation, 1-56, Oohama-Cho, Amagasaki-Shi, 660-0095, Japan. The batch number was 0309651L. DPPG-Na was kept at approximately −20° C. until use. The purity of DPPG-Na was 99.2%. A solution of DPPG-Na was made by dissolving 49.1 mg of DPPG-Na in 1 mL acetic acid/water 5% to yield a final concentration of 50 mg/mL.

Example 2

Preparation of Control Uncharged Lipoprotein Complexes

Control uncharged lipoprotein complexes consisting of proApo-AT (33 wt %) and sphingomyelin (67 wt %) were prepared as described below.

Formulations of control uncharged lipoprotein complexes were prepared by mixing 5.6 mL of proApoA-I at 25 mg/mL with approximately 5.6 mL of sphingomyelin at 50 mg/mL in 100 mL glass flask(s). The resulting mixture was filtered through a 0.22 μm nylon filter. The mixture was heated at approximately 50° C. and then frozen in liquid nitrogen under manual agitation. Immediately after freezing, the flasks were placed in a lyophilizer for 15 hours. After lyophilization, the flasks were placed under vacuum at approximately 40° C. for 4 hours. The resulting formulations were stored at approximately 4° C. until use.

Fourteen mL of a solution containing 140 mM NaCl and 20 mM NaHCO₃ was added to a glass flask containing a lyophilized formulation of a control uncharged lipoprotein complex. The resulting solution was adjusted to a basic pH by adding 0.75 mL IM NaOH in 20 mL of solution. The solution was agitated manually, heated at approximately 50° C., and then placed in an ultrasonic bath for at least one hour. The concentration of proApoA-1 in the resulting formulation was 10 mg/mL. The formulation(s) was injected into a HPLC system to check for the presence of uncharged lipoprotein complexes. FIG. 1 provides an example of a HPLC chromatogram for an uncharged lipoprotein complex made as described herein.

Example 3

Preparation of Test Charged Lipoprotein Complexes

Charged lipoprotein complexes consisting of proApoAI (33 wt %), sphingomyelin (65 wt %) and phosphatidylglycerol (2 wt %) were prepared as described below.

Formulations of charged lipoprotein complexes were prepared by mixing 5.6 mL of proApoA-I at 25 mg/mL with approximately 5.6 mL of sphingomyelin at 50 mg/mL, and approximately 0.15 mL of DPPG-NA at 50 mg/mL in a 100 mL glass flask(s) and then filtering the resulting mixture through a 0.22 μm nylon filter. The mixture was heated at approximately 50° C. and frozen in liquid nitrogen under manual agitation. Immediately after freezing, the flasks were placed in a lyophilizer for 15 hours. After lyophilization, the flasks were placed under vacuum at approximately 40° C. for 4 hours. The resulting formulation was stored at approximately 4° C. until use.

Fourteen mL of 140 mM NaCl and 20 mM NaHCO$_3$ was added to a glass flask containing the lyophilized formulation described above. The resulting solution was adjusted to a basic pH by adding 0.75 mL 1M NaOH in 20 mL of solution. The solution was agitated manually, heated at approximately 50° C., and then placed in an ultrasonic bath for at least one hour. The concentration of proApoA-I in the resulting formulation was 10 mg/mL. The formulation(s) was injected into a HPLC system to check for the presence of uncharged lipoprotein complexes. FIG. 2 provides an example of a HPLC chromatogram for a charged lipoprotein complex made as described herein.

Example 4

Animal Model System

New Zealand male rabbits weighing between 3 to 4 kg were used to test cholesterol mobilization by the uncharged and charged complexes described above. The animals were supplied by CEGAV, France and individually identified with a unique ear tattoo. The rabbits were housed in the Avogadro (France) animal facilities in individual cages. Animal housing and care complied with the recommendations of Directive 86/609/EEC. Animal facilities of Avogadro have the agreement number B 31 188 01 obtained from the French Veterinary Authorities. All animals was managed similarly and with due regard for their well-being according to prevailing practices and the current standard operating procedures (SOPs) at Avogadro. The equipment and animal houses were cleaned at appropriate intervals.

The animal room conditions were as follows: temperature: 22±2° C., relative humidity: 55±15%, and a 12 hour light/12 hour dark cycle. The temperature and relative humidity were recorded daily and stored with the raw data of the study. Each rabbit was observed once daily, any abnormal findings were recorded as observed, and reported to the Study Director.

Animals were acclimatized for at least 7 days before the beginning of the study. The animals received ad libitum a controlled pellet diet on a daily basis. Water was available ad libitum throughout the study.

Before administration of the complexes, the animals were fasted overnight. The animals were weighed just before administration of the complexes. The complexes were administered intravenously at a dosage rate of 15 mg/kg which corresponds to 1.5 mL/kg. The volume administered was based on weight. Feeding was resumed approximately 6 hours after the administration of the complexes. Treatment details recorded included dosage calculations, dose administered, date, and time of administration.

Prior to the collection of blood samples, the animals were fasted overnight. Blood samples were withdrawn from the jugular vein or from the marginal vein of the ear. Blood was withdrawn from the jugular vein using a syringe mounted with a needle with EDTA (approximately 1 mL of blood per sampling time). Immediately after collection, blood samples were kept at approximately 4° C. to avoid alteration of the blood sample. Blood specimens were centrifuged (3500 g, for 10 minutes at approximately 5° C.). Plasma specimens were separated and aliquoted (3 aliquots of at least 200 μL (aliquots A, B, C)) and stored at approximately −80° C. The remaining blood clot was discarded.

Example 5

Charged Lipoprotein Complexes Mobilize Cholesterol

Control lipoprotein complexes (formulation IIA) or charged lipoprotein complexes (formulation IIB) were prepared as described above and administered to rabbits (15 mg complex/kg body weight), two rabbits per group.

Blood samples (1 ml) were taken at pre-dose, 5 min, 15 min, 30 min, 1 h, 2 h, 3 h and 6 h after administration. Plasma samples were analyzed for total cholesterol, free cholesterol and triglyceride according to published methods (see, e.g., Usui, S., et al., 2002, J. Lipid Res., 43:805-14). Esterified cholesterol concentration was calculated by subtracting the free cholesterol content from the total cholesterol content. The free cholesterol in HDL results for each animal are illustrated in FIG. 3. The averaged values for the two animals comprising the control group (group BA) and the test group (group IIB) are illustrated in FIG. 4.

As expected, both the control and test lipoprotein complexes mobilized cholesterol, with the average of the test group showing increased mobilization as compared to the average of the control group.

All cited references are incorporated herein by reference in their entirety and for all purposes to the same extent as if each individual publication, patent or patent application was specifically and individually indicated to be incorporated herein by reference in its entirety for all purposes.

The citation of any publication is for its disclosure prior to the filing date and should not be construed as an admission that the present invention is not entitled to antedate such publication by virtue of prior invention.

Many modifications and variations of this invention can be made without departing from its spirit and scope, as will be apparent to those skilled in the art. The specific embodiments described are offered by way of example only, and the invention is to be limited only by the terms of the appended claims along with the full scope of equivalents to which such claims are entitled.

What is claimed is:

1. A charged lipoprotein complex comprising (i) an apolipoprotein fraction comprising at least one apolipoprotein, (ii) a lipid fraction comprising (a) sphingomyelin, (b) phosphatidylglycerol, and, optionally (c) lecithin, and (iii) a label, wherein the total amount of the phosphatidylglycerol is 3 wt % of the lipid fraction.

2. The charged lipoprotein complex of claim 1, wherein the label is a radiolabel.

3. The charged lipoprotein complex of claim 2, wherein the radiolabel is $^{125}$I, $^{14}$C, or $^{3}$H.

4. The charged lipoprotein complex of claim 1, wherein the label is a fluorescent label.

5. The charged lipoprotein complex of claim 1, wherein the label is an enzyme label.

6. The charged lipoprotein complex of claim 1, wherein the label is a dye.

7. The charged lipoprotein complex of claim 1, wherein the apolipoprotein fraction is labeled with the label.

8. The charged lipoprotein complex of claim 1, wherein the phosphatidylglycerol in the lipid fraction is labeled with the label.

9. The charged lipoprotein complex of claim 1, wherein the apolipoprotein fraction comprises an ApoA-I, a preproApoA-I or a proApoA-I.

10. The charged lipoprotein complex of claim 9, wherein the apolipoprotein fraction comprises preproApoA-I, proApoA-I, ApoA-I, preproApoA-I$_{Milano}$, proApoA-I$_{Milano}$, ApoA-I$_{Milano}$, preproApoA-I$_{Paris}$, proApoA-I$_{Paris}$, ApoA-I$_{Paris}$ or a mixture thereof.

11. The charged lipoprotein complex of claim 1, wherein the lipid fraction comprises sphingomyelin, the one or more negatively charged phospholipids phosphatidylglycerol, and lecithin.

12. The charged lipoprotein complex of claim 1, wherein the lipid:apolipoprotein molar ratio of the lipoprotein complex ranges from 2:1 to 200:1, where the value for the apolipoprotein is expressed in ApoA-I equivalents.

13. A pharmaceutical composition comprising the charged lipoprotein complex of claim 1 and a pharmaceutically acceptable carrier, diluent, and/or excipient.

* * * * *